United States Patent
Xie et al.

(10) Patent No.: US 7,388,103 B2
(45) Date of Patent: Jun. 17, 2008

(54) CYCLOPENTANE CARBOXYLATE COMPOUNDS, PROCESS AND INTERMEDIATES FOR PREPARING THE SAME AND USE THEREOF

(75) Inventors: Lunjia Xie, Beijing (CN); Hongbin Du, Beijing (CN); Zhibiao Hu, Beijing (CN); Tianyi Zhang, Beijing (CN); Siyuan Zhao, Beijing (CN); Xinsheng Wang, Beijing (CN)

(73) Assignees: China Petroleum & Chemical Corporation, Beijing (CN); Beijing Research Institute of Chemical Industry, Beijing (CN)

( * ) Notice: Subject to any disclaimer, the term of this patent is extended or adjusted under 35 U.S.C. 154(b) by 61 days.

(21) Appl. No.: 11/258,919

(22) Filed: Oct. 27, 2005

(65) Prior Publication Data

US 2006/0094843 A1    May 4, 2006

(30) Foreign Application Priority Data

Oct. 29, 2004    (CN) .................. 2004 1 0086289

(51) Int. Cl.
    C07C 69/74    (2006.01)
(52) U.S. Cl. ............ 560/121; 560/121; 560/122; 526/213
(58) Field of Classification Search ............ 560/121, 560/122; 526/213; 562/121, 122
    See application file for complete search history.

(56) References Cited

U.S. PATENT DOCUMENTS

| 4,544,717 A | 10/1985 | Mayr et al. |
| 5,468,704 A | 11/1995 | Morini et al. |

FOREIGN PATENT DOCUMENTS

| CN | 1446787 | 8/2003 |
| CN | 1490340 | 4/2004 |
| EP | 0 361 493 B1 | 11/1994 |
| EP | 0 045 977 B2 | 3/1995 |
| EP | 0 728 724 A1 | 8/1996 |
| WO | WO-98/56830 A | 12/1998 |
| WO | WO-00/26259 A | 5/2000 |
| WO | WO-03/022894 A1 | 3/2003 |

OTHER PUBLICATIONS

M.E.Dobson, J.Fearns, W.H.Perkin, □□Synthesis of cyclohexanone-3-caboxylic acid, □□J.Chem.Soc., vol. 95, 1909, pp. 2010-2017.*

Hariharan Venkatesan et al., *Journal of Organic Chemistry*, vol. 60, No. 4, (1995), pp. 1053-1059.
Toshio Sato et al., *Chemistry Letters*, vol. 10, (1988), pp. 1739-1742.
Chemistry Abstract 93: 46006, (1979), pp. 167-168.
Sigeru Torii et al., *Journal of Organic Chemistry*, vol. 44, No. 13, (1979), pp. 2303-2307.
K.H. Gibson et al., *Journal Of The Chemical Society*, vol. 21, (1972), pp. 2776-2787.
Homer Adkins et al., *Journal Of The American Chemical Society*, vol. 71, (1949), pp. 2965-2968.
Li Jia-hui et al., *Liaoning Chemical Industry*, vol. 31, No. 9, (Sep. 2002), whole document.
CN 1490340 A (Sinopec, et al.), (Apr. 21, 2004). see whole document.
CN 1446787 A (Sinopec et al.), (Oct. 8, 2003). see whole document.

* cited by examiner

*Primary Examiner*—Yvonne Eyler
*Assistant Examiner*—Sudhakar Katakam
(74) *Attorney, Agent, or Firm*—Birch, Stewart, Kolasch & Birch, LLP

(57) ABSTRACT

The present invention discloses cyclopentane carboxylate compounds. The 1-hydrocarbyl-2-acyloxy-cyclopentane carboxylates according to the invention have a general formula (I):

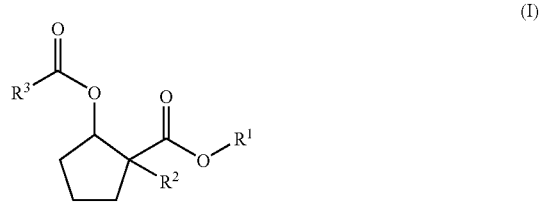

(I)

wherein groups $R^1$, $R^2$ and $R^3$, which are identical or different, are independently selected from the group consisting of linear or branched $C_1$-$C_{20}$alkyl, $C_3$-$C_{20}$cycloalkyl, $C_6$-$C_{20}$aryl, $C_7$-$C_{20}$alkaryl and $C_7$-$C_{20}$aralkyl. The present invention also discloses a process as well as intermediate compounds for preparing the compounds of formula (I), and use of the compounds (I) as electron donor in the preparation of catalysts for propylene polymerization.

19 Claims, No Drawings

CYCLOPENTANE CARBOXYLATE COMPOUNDS, PROCESS AND INTERMEDIATES FOR PREPARING THE SAME AND USE THEREOF

CROSS REFERENCE OF RELATED APPLICATION

The present application claims priority based on Chinese patent application No. 200410086289.X, filed on Oct. 29, 2004, which is incorporated herein by reference in its entirety and for all purposes.

TECHNICAL FIELD

The present invention relates to cyclopentane carboxylate compounds, to a process and intermediates for preparing the same, and to use thereof. More specifically, the present invention relates to 1-hydrocarbyl-2-acyloxy-cyclopentane carboxylate compounds (I), to process for preparing the same, to the intermediate 2-hydrocarbyl-2-hydrocarbyloxy-carbonylcyclopentanols (II), and to use of 1-hydrocarbyl-2-acyloxy-cyclopentane carboxylate compound (I).

BACKGROUND ART

It has been known to use a Ziegler-Natta catalyst containing a titanium compound and an electron donor compound supported on active magnesium halide in olefin polymerization. U.S. Pat. No. 4,544,717 teaches that stereospecificity of a catalyst can be improved by introducing an electron donor compound into a solid component containing a titanium compound. EP 0 045 977 discloses a polymerization catalyst having higher activity and stereospecificity, wherein phthalates are used as internal electron donor compound, silicone compounds containing at least one Si—OR bond (wherein R represents alkyl) are used as external electron donor compound, and aluminum alkyls are used as cocatalyst.

Many electron donor compounds useful in the preparation of Ziegler-Natta catalysts as well as catalysts for olefin polymerization comprising these electron donor compounds have been disclosed. For example, EP0361493 and EP0728724 disclose 1,3-diether compounds, CN1105671A discloses 1,3-diketone compounds, CN1236372A and CN1292800 discloses specific substituted malonate compounds, WO03022894 discloses diesters of maleic acid as electron donor compound. Additionally, CN1446787A and CN1490340A disclose γ-acyloxy-substituted ether compounds having a formula (III), and catalysts for propylene polymerization and exhibiting excellent performance can be prepared using said compounds as internal electron donor added during the preparation of solid component of catalytic system for olefin polymerization through a preparation process similar to that used in the preparation of N-Catalysts (trade name of polypropylene catalyst by Beijing Research Institute of Chemical Industry, SINOPEC, China).

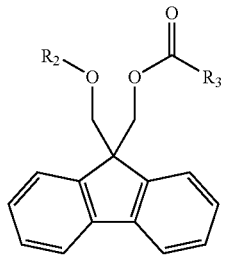

(III)

However, known literatures disclose neither 1-hydrocarbyl-2-acyloxy-cyclopentane carboxylate compounds having a general formula (I) as described hereinafter as well as a process for the preparation thereof nor use of the compounds of the formula (I) as electron donor in the preparation of catalysts for olefin polymerization.

SUMMARY OF THE INVENTION

An object of the invention is to provide novel cyclopentane carboxylate compounds, i.e. 1-hydrocarbyl-2-acyloxy-cyclopentane carboxylate compounds of formula (I).

Another object of the invention is to provide a process for preparing the compounds of the formula (I) as well as the intermediates used therein.

Still another object of the invention is to provide use of said compounds in the preparation of olefin polymerization catalysts, especially Ziegler-Natta type polypropylene catalysts.

DETAILED DESCRIPTION OF THE PREFERRED EMBODIMENTS

The cyclopentane carboxylate compounds according to the invention, 1-hydrocarbyl-2-acyloxy-cyclopentane carboxylate compounds, have a structure represented by the general formula (I):

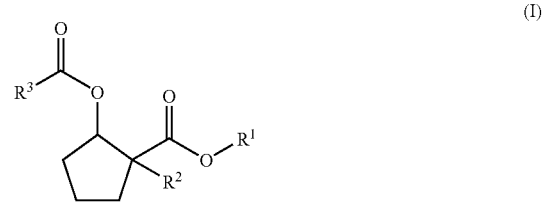

wherein groups $R^1$, $R^2$ and $R^3$, which are identical or different, are independently selected from the group consisting of linear or branched $C_1$-$C_{20}$alkyl, $C_3$-$C_{20}$cycloalkyl, $C_6$-$C_{20}$aryl, $C_7$-$C_{20}$alkaryl and $C_7$-$C_{20}$aralkyl.

$R^1$ is preferably $C_1$-$C_8$alkyl, and more preferably methyl, ethyl or iso-butyl; $R^2$ is preferably selected from the group consisting of $C_1$-$C_{10}$alkyl, $C_3$-$C_{10}$cycloalkyl, $C_4$-$C_9$alkylcycloalkyl, $C_4$-$C_9$cycloalkylalkyl, $C_6$-$C_{10}$aryl, $C_7$-$C_{10}$alkaryl and $C_7$-$C_{10}$aralkyl; and $R^3$ is preferably selected from the group consisting of $C_1$-$C_{10}$alkyl, $C_3$-$C_{10}$cycloalkyl, $C_6$-$C_{10}$aryl, $C_7$-$C_{10}$alkaryl and $C_7$-$C_{10}$aralkyl.

When $R^1$ is methyl, ethyl or iso-butyl, $R^2$ is preferably selected from the group consisting of $C_1$-$C_{10}$alkyl, $C_3$-$C_8$cycloalkyl, $C_5$-$C_7$cycloallylmethyl, $C_6$-$C_9$aryl, $C_7$-$C_{10}$alkaryl and $C_7$-$C_{10}$aralkyl, and more preferably selected from the group consisting of $C_1$-$C_6$alkyl, $C_5$-$C_8$cycloalkyl, $C_6$-$C_9$aryl, benzyl, p-methylbenzyl and phenethyl; and $R^3$ is preferably selected from the group consisting of $C_1$-$C_4$alkyl, $C_5$-$C_8$cycloalkyl, phenyl, p-methylphenyl, o-methylphenyl, m-methylphenyl and benzyl.

More preferably, $R^1$ is methyl or ethyl; $R^2$ is methyl, ethyl, n-propyl, iso-propyl, n-butyl, iso-butyl, n-pentyl, iso-pentyl, n-hexyl, benzyl, p-methylbenzyl or phenethyl; and $R^3$ is methyl, ethyl, n-propyl, iso-propyl, n-butyl, phenyl, p-methylphenyl, o-methylphenyl, m-methylphenyl or benzyl.

Examples of the cyclopentane carboxylate compounds according to the invention include, but are not limited to,
ethyl 1-benzyl-2-benzoyloxy-cyclopentane carboxylate;

ethyl 1-benzyl-2-p-methylbenzoyloxy-cyclopentane carboxylate;
ethyl 1-benzyl-2-m-methylbenzoyloxy-cyclopentane carboxylate;
ethyl 1-benzyl-2-o-methylbenzoyloxy-cyclopentane carboxylate;
methyl 1-p-methylbenzyl-2-benzoyloxy-cyclopentane carboxylate;
methyl 1-p-methylbenzyl-2-p-methylbenzoyloxy-cyclopentane carboxylate;
methyl 1-p-methylbenzyl-2-m-methylbenzoyloxy-cyclopentane carboxylate;
methyl 1-p-methylbenzyl-2-o-methylbenzoyloxy-cyclopentane carboxylate;
ethyl 1-n-butyl-2-benzoyloxy-cyclopentane carboxylate;
ethyl 1-n-butyl-2-p-methylbenzoyloxy-cyclopentane carboxylate;
ethyl 1-n-hexyl-2-benzoyloxy-cyclopentane carboxylate;
ethyl 1-n-hexyl-2-p-methylbenzoyloxy-cyclopentane carboxylate;
ethyl 1-n-hexyl-2-m-methylbenzoyloxy-cyclopentane carboxylate;
ethyl 1-n-hexyl-2-o-methylbenzoyloxy-cyclopentane carboxylate;
ethyl 1-ethyl-2-acetoxy cyclopentane carboxylate;
ethyl 1-ethyl-2-benzoyloxy-cyclopentane carboxylate;
ethyl 1-ethyl-2-o-methylbenzoyloxy-cyclopentane carboxylate;
ethyl 1-n-propyl-2-benzoyloxy-cyclopentane carboxylate;
ethyl 1-n-propyl-2-o-methylbenzoyloxy-cyclopentane carboxylate;
ethyl 1-n-propyl-2-m-methylbenzoyloxy-cyclopentane carboxylate;
ethyl 1-n-propyl-2-p-methylbenzoyloxy-cyclopentane carboxylate;
ethyl 1-n-butyl-2-m-methylbenzoyloxy-cyclopentane carboxylate;
ethyl 1-n-butyl-2-o-methylbenzoyloxy-cyclopentane carboxylate;
ethyl 1-iso-butyl-2-benzoyloxy-cyclopentane carboxylate;
ethyl 1-iso-butyl-2-o-methylbenzoyloxy-cyclopentane carboxylate;
ethyl 1-iso-butyl-2-m-methylbenzoyloxy-cyclopentane carboxylate;
ethyl 1-iso-pentyl-2-benzoyloxy-cyclopentane carboxylate;
methyl 1-methyl-2-acetoxy-cyclopentane carboxylate;
methyl 1-ethyl-2-acetoxy-cyclopentane carboxylate;
methyl 1-n-propyl-2-acetoxy-cyclopentane carboxylate;
methyl 1-iso-propyl-2-acetoxy-cyclopentane carboxylate;
methyl 1-n-butyl-2-acetoxy-cyclopentane carboxylate;
methyl 1-iso-butyl-2-acetoxy-cyclopentane carboxylate;
methyl 1-n-pentyl-2-acetoxy-cyclopentane carboxylate;
methyl 1-iso-pentyl-2-acetoxy-cyclopentane carboxylate;
methyl 1-n-hexyl-2-acetoxy-cyclopentane carboxylate;
methyl 1-cyclopentyl-2-acetoxy-cyclopentane carboxylate;
methyl 1-cyclohexyl-2-acetoxy-cyclopentane carboxylate;
methyl 1-phenyl-2-acetoxy-cyclopentane carboxylate;
methyl 1-p-methylphenyl-2-acetoxy-cyclopentane carboxylate;
methyl 1-benzyl-2-acetoxy-cyclopentane carboxylate;
methyl 1-phenethyl-2-acetoxy-cyclopentane carboxylate;
methyl 1-p-methylbenzyl-2-acetoxy-cyclopentane carboxylate;
ethyl 1-methyl-2-acetoxy-cyclopentane carboxylate;
ethyl 1-n-propyl-2-acetoxy-cyclopentane carboxylate;
ethyl 1-iso-propyl-2-acetoxy-cyclopentane carboxylate;
ethyl 1-n-butyl-2-acetoxy-cyclopentane carboxylate;
ethyl 1-iso-butyl-2-acetoxy-cyclopentane carboxylate;
ethyl 1-n-pentyl-2-acetoxy-cyclopentane carboxylate;
ethyl 1-iso-pentyl-2-acetoxy-cyclopentane carboxylate;
ethyl 1-n-hexyl-2-acetoxy-cyclopentane carboxylate;
ethyl 1-cyclopentyl-2-acetoxy-cyclopentane carboxylate;
ethyl 1-cyclohexyl-2-acetoxy-cyclopentane carboxylate;
ethyl 1-phenyl-2-acetoxy-cyclopentane carboxylate;
ethyl 1-p-methylphenyl-2-acetoxy-cyclopentane carboxylate;
ethyl 1-benzyl-2-acetoxy-cyclopentane carboxylate;
ethyl 1-phenethyl-2-acetoxy-cyclopentane carboxylate;
ethyl 1-p-methylbenzyl-2-acetoxy-cyclopentane carboxylate;
iso-butyl 1-methyl-2-acetoxy-cyclopentane carboxylate;
iso-butyl 1-ethyl-2-acetoxy-cyclopentane carboxylate;
iso-butyl 1-n-propyl-2-acetoxy-cyclopentane carboxylate;
iso-butyl 1-iso-propyl-2-acetoxy-cyclopentane carboxylate;
iso-butyl 1-n-butyl-2-acetoxy-cyclopentane carboxylate;
iso-butyl 1-iso-butyl-2-acetoxy-cyclopentane carboxylate;
iso-butyl 1-n-pentyl-2-acetoxy-cyclopentane carboxylate;
iso-butyl 1-iso-pentyl-2-acetoxy-cyclopentane carboxylate;
iso-butyl 1-n-hexyl-2-acetoxy-cyclopentane carboxylate;
iso-butyl 1-cyclopentyl-2-acetoxy-cyclopentane carboxylate;
iso-butyl 1-cyclohexyl-2-acetoxy-cyclopentane carboxylate;
iso-butyl 1-phenyl-2-acetoxy-cyclopentane carboxylate;
iso-butyl 1-p-methylphenyl-2-acetoxy-cyclopentane carboxylate;
iso-butyl 1-benzyl-2-acetoxy-cyclopentane carboxylate;
iso-butyl 1-phenethyl-2-acetoxy-cyclopentane carboxylate;
iso-butyl 1-p-methylbenzyl-2-acetoxy-cyclopentane carboxylate;
methyl 1-methyl-2-benzoyloxy-cyclopentane carboxylate;
methyl 1-ethyl-2-benzoyloxy-cyclopentane carboxylate;
methyl 1-n-propyl-2-benzoyloxy-cyclopentane carboxylate;
methyl 1-iso-propyl-2-benzoyloxy-cyclopentane carboxylate;
methyl 1-n-butyl-2-benzoyloxy-cyclopentane carboxylate;
methyl 1-iso-butyl-2-benzoyloxy-cyclopentane carboxylate;
methyl 1-n-pentyl-2-benzoyloxy-cyclopentane carboxylate;
methyl 1-iso-pentyl-2-benzoyloxy-cyclopentane carboxylate;
methyl 1-n-hexyl-2-benzoyloxy-cyclopentane carboxylate;
methyl 1-cyclopentyl-2-benzoyloxy-cyclopentane carboxylate;
methyl 1-cyclohexyl-2-benzoyloxy-cyclopentane carboxylate;
methyl 1-phenyl-2-benzoyloxy-cyclopentane carboxylate;

methyl 1-p-methylphenyl-2-benzoyloxy-cyclopentane carboxylate;
methyl 1-benzyl-2-benzoyloxy-cyclopentane carboxylate;
methyl 1-phenethyl-2-benzoyloxy-cyclopentane carboxylate;
ethyl 1-methyl-2-benzoyloxy-cyclopentane carboxylate;
ethyl 1-iso-propyl-2-benzoyloxy-cyclopentane carboxylate;
ethyl 1-n-pentyl-2-benzoyloxy-cyclopentane carboxylate;
ethyl 1-cyclopentyl-2-benzoyloxy-cyclopentane carboxylate;
ethyl 1-cyclohexyl-2-benzoyloxy-cyclopentane carboxylate;
ethyl 1-p-methylphenyl-2-benzoyloxy-cyclopentane carboxylate;
ethyl 1-benzyl-2-benzoyloxy-cyclopentane carboxylate;
ethyl 1-phenethyl-2-benzoyloxy-cyclopentane carboxylate;
ethyl 1-p-methylbenzyl-2-benzoyloxy-cyclopentane carboxylate;
iso-butyl 1-methyl-2-benzoyloxy-cyclopentane carboxylate;
iso-butyl 1-ethyl-2-benzoyloxy-cyclopentane carboxylate;
iso-butyl 1-n-propyl-2-benzoyloxy-cyclopentane carboxylate;
iso-butyl 1-iso-propyl-2-benzoyloxy-cyclopentane carboxylate;
iso-butyl 1-n-butyl-2-benzoyloxy-cyclopentane carboxylate;
iso-butyl 1-iso-butyl-2-benzoyloxy-cyclopentane carboxylate;
iso-butyl 1-n-pentyl-2-benzoyloxy-cyclopentane carboxylate;
iso-butyl 1-iso-pentyl-2-benzoyloxy-cyclopentane carboxylate;
iso-butyl 1-n-hexyl-2-benzoyloxy-cyclopentane carboxylate;
iso-butyl 1-cyclopentyl-2-benzoyloxy-cyclopentane carboxylate;
iso-butyl 1-cyclohexyl-2-benzoyloxy-cyclopentane carboxylate;
iso-butyl 1-phenyl-2-benzoyloxy-cyclopentane carboxylate;
iso-butyl 1-p-methylphenyl-2-benzoyloxy-cyclopentane carboxylate;
iso-butyl 1-benzyl-2-benzoyloxy-cyclopentane carboxylate;
iso-butyl 1-phenethyl-2-benzoyloxy-cyclopentane carboxylate;
iso-butyl 1-p-methylbenzyl-2-benzoyloxy-cyclopentane carboxylate;
methyl 1-methyl-2-p-methylbenzoyloxy-cyclopentane carboxylate;
methyl 1-ethyl-2-p-methylbenzoyloxy-cyclopentane carboxylate;
methyl 1-n-propyl-2-p-methylbenzoyloxy-cyclopentane carboxylate;
methyl 1-iso-propyl-2-p-methylbenzoyloxy-cyclopentane carboxylate;
methyl 1-n-butyl-2-p-methylbenzoyloxy-cyclopentane carboxylate;
methyl 1-iso-butyl-2-p-methylbenzoyloxy-cyclopentane carboxylate;
methyl 1-n-pentyl-2-p-methylbenzoyloxy-cyclopentane carboxylate;
methyl 1-iso-pentyl-2-p-methylbenzoyloxy-cyclopentane carboxylate;
methyl 1-n-hexyl-2-p-methylbenzoyloxy-cyclopentane carboxylate;
methyl 1-cyclopentyl-2-p-methylbenzoyloxy-cyclopentane carboxylate;
methyl 1-cyclohexyl-2-p-methylbenzoyloxy-cyclopentane carboxylate;
methyl 1-phenyl-2-p-methylbenzoyloxy-cyclopentane carboxylate;
methyl 1-p-methylphenyl-2-p-methylbenzoyloxy-cyclopentane carboxylate;
methyl 1-benzyl-2-p-methylbenzoyloxy-cyclopentane carboxylate;
methyl 1-phenethyl-2-p-methylbenzoyloxy-cyclopentane carboxylate;
ethyl 1-methyl-2-p-methylbenzoyloxy-cyclopentane carboxylate;
ethyl 1-ethyl-2-p-methylbenzoyloxy-cyclopentane carboxylate;
ethyl 1-iso-propyl-2-p-methylbenzoyloxy-cyclopentane carboxylate;
ethyl 1-iso-butyl-2-p-methylbenzoyloxy-cyclopentane carboxylate;
ethyl 1-n-pentyl-2-p-methylbenzoyloxy-cyclopentane carboxylate;
ethyl 1-iso-pentyl-2-p-methylbenzoyloxy-cyclopentane carboxylate;
ethyl 1-cyclopentyl-2-p-methylbenzoyloxy-cyclopentane carboxylate;
ethyl 1-cyclohexyl-2-p-methylbenzoyloxy-cyclopentane carboxylate;
ethyl 1-phenyl-2-p-methylbenzoyloxy-cyclopentane carboxylate;
ethyl 1-p-methylphenyl-2-p-methylbenzoyloxy-cyclopentane carboxylate;
ethyl 1-phenethyl-2-p-methylbenzoyloxy-cyclopentane carboxylate;
ethyl 1-p-methylbenzyl-2-p-methylbenzoyloxy-cyclopentane carboxylate;
iso-butyl 1-methyl-2-p-methylbenzoyloxy-cyclopentane carboxylate;
iso-butyl 1-ethyl-2-p-methylbenzoyloxy-cyclopentane carboxylate;
iso-butyl 1-n-propyl-2-p-methylbenzoyloxy-cyclopentane carboxylate;
iso-butyl 1-iso-propyl-2-p-methylbenzoyloxy-cyclopentane carboxylate;
iso-butyl 1-n-butyl-2-p-methylbenzoyloxy-cyclopentane carboxylate;
iso-butyl 1-iso-butyl-2-p-methylbenzoyloxy-cyclopentane carboxylate;
iso-butyl 1-n-pentyl-2-p-methylbenzoyloxy-cyclopentane carboxylate;
iso-butyl 1-iso-pentyl-2-p-methylbenzoyloxy-cyclopentane carboxylate;
iso-butyl 1-n-hexyl-2-p-methylbenzoyloxy-cyclopentane carboxylate;
iso-butyl 1-cyclopentyl-2-p-methylbenzoyloxy-cyclopentane carboxylate;
iso-butyl 1-cyclohexyl-2-p-methylbenzoyloxy-cyclopentane carboxylate;
iso-butyl 1-phenyl-2-p-methylbenzoyloxy-cyclopentane carboxylate;
iso-butyl 1-p-methylphenyl-2-p-methylbenzoyloxy-cyclopentane carboxylate;

iso-butyl 1-benzyl-2-p-methylbenzoyloxy-cyclopentane carboxylate;
iso-butyl 1-phenethyl-2-p-methylbenzoyloxy-cyclopentane carboxylate;
iso-butyl 1-p-methylbenzyl-2-p-methylbenzoyloxy-cyclopentane carboxylate;
methyl 1-methyl-2-o-methylbenzoyloxy-cyclopentane carboxylate;
methyl 1-ethyl-2-o-methylbenzoyloxy-cyclopentane carboxylate;
methyl 1-n-propyl-2-o-methylbenzoyloxy-cyclopentane carboxylate;
methyl 1-iso-propyl-2-o-methylbenzoyloxy-cyclopentane carboxylate;
methyl 1-n-butyl-2-o-methylbenzoyloxy-cyclopentane carboxylate;
methyl 1-iso-butyl-2-o-methylbenzoyloxy-cyclopentane carboxylate;
methyl 1-n-pentyl-2-o-methylbenzoyloxy-cyclopentane carboxylate;
methyl 1-iso-pentyl-2-o-methylbenzoyloxy-cyclopentane carboxylate;
methyl 1-n-hexyl-2-o-methylbenzoyloxy-cyclopentane carboxylate;
methyl 1-cyclopentyl-2-o-methylbenzoyloxy-cyclopentane carboxylate;
methyl 1-cyclohexyl-2-o-methylbenzoyloxy-cyclopentane carboxylate;
methyl 1-phenyl-2-o-methylbenzoyloxy-cyclopentane carboxylate;
methyl 1-p-methylphenyl-2-o-methylbenzoyloxy-cyclopentane carboxylate;
methyl 1-benzyl-2-o-methylbenzoyloxy-cyclopentane carboxylate;
methyl 1-phenethyl-2-o-methylbenzoyloxy-cyclopentane carboxylate;
ethyl 1-methyl-2-o-methylbenzoyloxy-cyclopentane carboxylate;
ethyl 1-iso-propyl-2-o-methylbenzoyloxy-cyclopentane carboxylate;
ethyl 1-n-pentyl-2-o-methylbenzoyloxy-cyclopentane carboxylate;
ethyl 1-iso-pentyl-2-o-methylbenzoyloxy-cyclopentane carboxylate;
ethyl 1-cyclopentyl-2-o-methylbenzoyloxy-cyclopentane carboxylate;
ethyl 1-cyclohexyl-2-o-methylbenzoyloxy-cyclopentane carboxylate;
ethyl 1-phenyl-2-o-methylbenzoyloxy-cyclopentane carboxylate;
ethyl 1-p-methylphenyl-2-o-methylbenzoyloxy-cyclopentane carboxylate;
ethyl 1-phenethyl-2-o-methylbenzoyloxy-cyclopentane carboxylate;
ethyl 1-p-methylbenzyl-2-o-methylbenzoyloxy-cyclopentane carboxylate;
iso-butyl 1-methyl-2-o-methylbenzoyloxy-cyclopentane carboxylate;
iso-butyl 1-ethyl-2-o-methylbenzoyloxy-cyclopentane carboxylate;
iso-butyl 1-n-propyl-2-o-methylbenzoyloxy-cyclopentane carboxylate;
iso-butyl 1-iso-propyl-2-o-methylbenzoyloxy-cyclopentane carboxylate;
iso-butyl 1-n-butyl-2-o-methylbenzoyloxy-cyclopentane carboxylate;
iso-butyl 1-iso-butyl-2-o-methylbenzoyloxy-cyclopentane carboxylate;
iso-butyl 1-n-pentyl-2-o-methylbenzoyloxy-cyclopentane carboxylate;
iso-butyl 1-iso-pentyl-2-o-methylbenzoyloxy-cyclopentane carboxylate;
iso-butyl 1-n-hexyl-2-o-methylbenzoyloxy-cyclopentane carboxylate;
iso-butyl 1-cyclopentyl-2-o-methylbenzoyloxy-cyclopentane carboxylate;
iso-butyl 1-cyclohexyl-2-o-methylbenzoyloxy-cyclopentane carboxylate;
iso-butyl 1-phenyl-2-o-methylbenzoyloxy-cyclopentane carboxylate;
iso-butyl 1-p-methylphenyl-2-o-methylbenzoyloxy-cyclopentane carboxylate;
iso-butyl 1-benzyl-2-o-methylbenzoyloxy-cyclopentane carboxylate;
iso-butyl 1-phenethyl-2-o-methylbenzoyloxy-cyclopentane carboxylate;
iso-butyl 1-p-methylbenzyl-2-o-methylbenzoyloxy-cyclopentane carboxylate;
methyl 1-methyl-2-m-methylbenzoyloxy-cyclopentane carboxylate;
methyl 1-ethyl-2-m-methylbenzoyloxy-cyclopentane carboxylate;
methyl 1-n-propyl-2-m-methylbenzoyloxy-cyclopentane carboxylate;
methyl 1-iso-propyl-2-m-methylbenzoyloxy-cyclopentane carboxylate;
methyl 1-n-butyl-2-m-methylbenzoyloxy-cyclopentane carboxylate;
methyl 1-iso-butyl-2-m-methylbenzoyloxy-cyclopentane carboxylate;
methyl 1-n-pentyl-2-m-methylbenzoyloxy-cyclopentane carboxylate;
methyl 1-iso-pentyl-2-m-methylbenzoyloxy-cyclopentane carboxylate;
methyl 1-n-hexyl-2-m-methylbenzoyloxy-cyclopentane carboxylate;
methyl 1-cyclopentyl-2-m-methylbenzoyloxy-cyclopentane carboxylate;
methyl 1-cyclohexyl-2-m-methylbenzoyloxy-cyclopentane carboxylate;
methyl 1-phenyl-2-m-methylbenzoyloxy-cyclopentane carboxylate;
methyl 1-p-methylphenyl-2-m-methylbenzoyloxy-cyclopentane carboxylate;
methyl 1-benzyl-2-m-methylbenzoyloxy-cyclopentane carboxylate;
methyl 1-phenethyl-2-m-methylbenzoyloxy-cyclopentane carboxylate,
ethyl 1-methyl-2-m-methylbenzoyloxy-cyclopentane carboxylate;
ethyl 1-ethyl-2-m-methylbenzoyloxy-cyclopentane carboxylate;
ethyl 1-iso-propyl-2-m-methylbenzoyloxy-cyclopentane carboxylate;
ethyl 1-n-pentyl-2-m-methylbenzoyloxy-cyclopentane carboxylate;
ethyl 1-iso-pentyl-2-m-methylbenzoyloxy-cyclopentane carboxylate;
ethyl 1-cyclopentyl-2-m-methylbenzoyloxy-cyclopentane carboxylate;
ethyl 1-cyclohexyl-2-m-methylbenzoyloxy-cyclopentane carboxylate;

ethyl 1-phenyl-2-m-methylbenzoyloxy-cyclopentane carboxylate;
ethyl 1-p-methylphenyl-2-m-methylbenzoyloxy-cyclopentane carboxylate;
ethyl 1-phenethyl-2-m-methylbenzoyloxy-cyclopentane carboxylate;
ethyl 1-p-methylbenzyl-2-m-methylbenzoyloxy-cyclopentane carboxylate;
iso-butyl 1-methyl-2-m-methylbenzoyloxy-cyclopentane carboxylate;
iso-butyl 1-ethyl-2-m-methylbenzoyloxy-cyclopentane carboxylate;
iso-butyl 1-n-propyl-2-m-methylbenzoyloxy-cyclopentane carboxylate;
iso-butyl 1-iso-propyl-2-m-methylbenzoyloxy-cyclopentane carboxylate;
iso-butyl 1-n-butyl-2-m-methylbenzoyloxy-cyclopentane carboxylate;
iso-butyl 1-iso-butyl-2-m-methylbenzoyloxy-cyclopentane carboxylate;
iso-butyl 1-n-pentyl-2-m-methylbenzoyloxy-cyclopentane carboxylate;
iso-butyl 1-iso-pentyl-2-m-methylbenzoyloxy-cyclopentane carboxylate;
iso-butyl 1-n-hexyl-2-m-methylbenzoyloxy-cyclopentane carboxylate;
iso-butyl 1-cyclopentyl-2-m-methylbenzoyloxy-cyclopentane carboxylate;
iso-butyl 1-cyclohexyl-2-m-methylbenzoyloxy-cyclopentane carboxylate;
iso-butyl 1-phenyl-2-m-methylbenzoyloxy-cyclopentane carboxylate;
iso-butyl 1-p-methylphenyl-2-m-methylbenzoyloxy-cyclopentane carboxylate;
iso-butyl 1-benzyl-2-m-methylbenzoyloxy-cyclopentane carboxylate;
iso-butyl 1-phenethyl-2-m-methylbenzoyloxy-cyclopentane carboxylate;
iso-butyl 1-p-methylbenzyl-2-m-methylbenzoyloxy-cyclopentane carboxylate.

The process for preparing 1-hydrocarbyl-2-acyloxy-cyclopentane carboxylate compounds of the formula (I) according to the invention comprises, in turn, the steps of:

1) synthesizing 2-hydrocarbyl-2-hydrocarbyloxycarbonyl-cyclopentanol intermediate having a general formula (II)

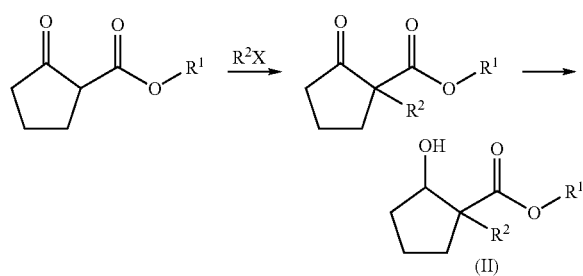

wherein $R^1$ and $R^2$ are as defined in the general formula (I) and X represents halogen atom, by hydrocarbylating 2-oxocyclopentane carboxylate on α-carbon with a halohydrocarbon ($R^2X$) in the presence of a base and an aprotic solvent to form 1-hydrocarbyl-2-oxocyclopentane carboxylate, and then selectively reducing the 1-hydrocarbyl-2-oxocyclopentane carboxylate to form 2-hydrocarbyl-2-hydrocarbyloxycarbonyl-cyclopentanol (also known as 1-hydrocarbyl-2-hydroxy-cyclopentane carboxylate) of the formula (II); and 2) synthesizing 1-hydrocarbyl-2-acyloxy-cyclopentane carboxylate compound of the formula (I)

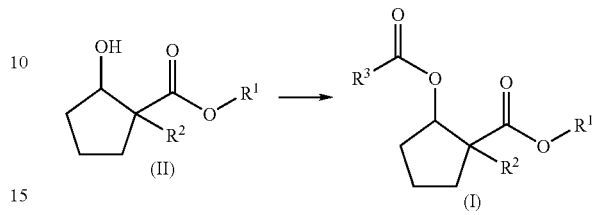

by acylating 2-hydrocarbyl-2-hydrocarbyloxycarbonyl-cyclopentanol of the formula (II) obtained in step 1) with an acyl halide or an anhydride in the presence of an aprotic solvent through conventional acylating methods (see, for example, Vogel's Textbook of Practical Organic Chemistry 5th ed., 1988), to form the corresponding 1-hydrocarbyl-2-acyloxy-cyclopentane carboxylate compound of the formula (I).

The starting material, 2-oxocyclopentane carboxylate, used in the step 1) may be prepared through known synthesis methods disclosed in the literatures (see, for example, Org. Synth., Coll. Vol., 2, 116(1943)).

In the step 1), a phase-transfer catalyst may or may not be used depending on the kind of the used halohydrocarbon ($R^2X$). When the halohydrocarbon ($R^2X$) used in the hydrocarbylation on the α-carbon is a branched- or cyclic group-containing haloalkane, phase-transfer catalyst, such as benzyl triethyl ammonium chloride, tetra-n-butyl ammonium bromide or combination thereof, is preferably used. In general, known operation methods for hydrocarbylation on carbon atom (for example, the method disclosed in Tetrahedron 32, 2979 (1976)) can be followed with aprotic solvent used. The aprotic solvent is preferably selected from the group consisting of acetone; N,N-dimethyl formamide; dimethyl sulfoxide; tetrahydrofuran; aliphatic hydrocarbons, such as pentane and hexane; and aromatic hydrocarbons, such as benzene, toluene, and xylene; and combination thereof, and more preferably aprotic polar solvents, such as acetone; N,N-dimethyl formamide; dimethyl sulfoxide; and combination thereof. The base is preferably selected from the group consisting of an alkali metal, an alkaline earth metal, a hydride of alkali metal or alkaline earth metal, a carbonate of alkali metal or alkaline earth metal, and combination thereof, and more preferably a carbonate of alkali metal.

In the hydrocarbylation on the α-carbon of the step 1), molar ratio of the 2-oxocyclopentane carboxylate to the halohydrocarbon ($R^2X$) is preferably in a range of from 1:0.5 to 1:5, and more preferably from 1:1 to 1:2; and molar ratio of the 2-oxocyclopentane carboxylate to the base is preferably in a range of from 1:0.5 to 1:5, and more preferably from 1:1.2 to 1:3. Reaction pressure is preferably in a range of from atmosphere pressure to 3 atm, and more preferably atmosphere pressure. The reaction is preferably carried out at a temperature of from 10 to 190° C., and more preferably from room temperature to 60° C. Reaction time is preferably in a range of from 1 to 24 hours, and the exact reaction time can be determined by GC-MS analysis on the reaction liquid.

In the step 1), the 1-hydrocarbyl-2-oxocyclopentane carboxylate obtained can be reduced by a reducing agent in an alcoholic solvent, to further form a compound of the general formula (II). The used reducing agent can be selected from the group consisting of metal borohydrides, such as lithium borohydride, sodium borohydride, potassium borohydride, and zinc borohydride; aluminum alkoxides, such as aluminum isopropoxide; and combination thereof. More preferably, if a metal borohydride is used, then sodium borohydride or potassium borohydride as well as methanol solvent is preferably used; and if an aluminum alkoxide is used, then aluminum isopropoxide as well as iso-propanol solvent is preferably used.

In the reduction reaction of the step 1), molar ratio of the 1-hydrocarbyl-2-oxocyclopentane carboxylate to the reducing agent is preferably in a range of from 1:0.5 to 1:2, and more preferably from 1:1.2 to 1:2. Reaction pressure is preferably in a range of from atmosphere pressure to 3 atm, and more preferably atmosphere pressure. The reaction is preferably carried out at a temperature of from −20 to 100° C., and more preferably from −10 to 78° C. Reaction time is preferably in a range of from 0.1 to 10 hours.

If the reduction reaction employs sodium borohydride as reducing agent and methanol as solvent, the reaction is carried out at a temperature of from −20 to 65° C., and preferably from −10 to 40° C.; molar ratio of the 1-hydrocarbyl-2-oxocyclopentane carboxylate to sodium borohydride is preferably in a range of from 1:1 to 1:2, and more preferably 1:1.2; reaction pressure is preferably in a range of from atmosphere pressure to 3 atm, and more preferably atmosphere pressure; the reactants are preferably added in such a way that sodium borohydride is batchwise added to a solution of 1-hydrocarbyl-2-oxocyclopentane carboxylate in methanol, and reaction time is preferably in a range of from 0.5 to 2 hours.

In the step 1), the 1-hydrocarbyl-2-oxocyclopentane carboxylate obtained can also be selectively reduced in a solvent under catalytic hydrogenation conditions, to form a compound of the general formula (II) (see, for example, J. Fuhrhop, G Penzlin, Organic Synthesis-Concepts, Methods, Starting Materials, verlag chemie, 90, 1983). The used catalyst contains generally a transition metal element, and can be selected from the group consisting of nickel-containing catalysts such as Raney nickel, palladium-containing catalysts, Adams' catalyst, and ruthenium-containing catalysts. Adams' catalyst is preferred. Reaction pressure is preferably in a range of from 1 to 10 atm, and more preferably from 1 to 3 atm. The reaction is preferably carried out at a temperature of from 0 to 200° C., and more preferably from 10° C. to room temperature. The solvent is preferably alcohols (for example, methanol, ethanol, etc.), ethers (for example, tetrahydrofuran, 1,2-dimethoxy ethane, etc.), and esters (for example, ethyl acetate, butyl acetate), or combination thereof, and more preferably ethanol. Depending on activity of a prepared catalyst and amount of the catalyst, reaction time is preferably from 0.5 to 24 hours. The catalyst is generally used in an amount of from 0.1 to 5 percent by mole with respect to the reactant.

In the step 2), according to conventional acylation processes, the intermediate (II) is acylated with an acyl halide

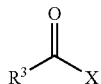

as acylating agent in the presence of a base, or with an acid anhydride

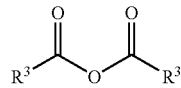

as acylating agent in the presence of an acid (wherein $R^3$ is as defined in the general formula (I); and X represents Cl, Br or I), to form 1-hydrocarbyl-2-acyloxy-cyclopentane carboxylate compound. The acylating agent is preferably acyl halide. The molar ratio of the acylating agent to the intermediate (II) is preferably in a range of from 1:1 to 15:1, and more preferably from 1.5:1 to 5:1. The base is preferably pyridine or triethyl amine, and molar ratio of the base to the acylating agent is preferably in a range of from 1:1 to 10:1, and more preferably from 1:1 to 3:1. The solvent used in the acylation reaction is generally aprotic solvent, and can be selected from the group consisting of pyridine, tetrahydrofuran, haloalkanes (such as methylene chloride, chloroform, etc.), aliphatic hydrocarbons (such as pentane, hexane, etc.) and aromatic hydrocarbons (such as benzene, toluene, xylene, etc.), and combination thereof, with methylene chloride and chloroform being preferred. Reaction temeperature is preferably in a range of from −20 to 200° C., and preferably from −5 to 100° C. In the step 2), reaction pressure is preferably in a range of from atmosphere pressure to 3 atm, and more preferably atmosphere pressure.

If an acid anhydride is used as the acylating agent, the acylation reaction is carried out in the presence of an acid catalyst, and commonly used acid catalysts include sulfuric acid, zinc chloride, etc., with a catalytic amount of sulfuric acid being preferred (see, for example, Vogel's Textbook of Practical Organic Chemistry 5th ed., 1988).

The lasting time of the acylation reaction can be varied or adjusted depending on the used intermediate (II) and the acylating agent, and the reaction can be monitored by thin-layer chromatography. Upon the completion of the reaction, 1-hydrocarbyl-2-acyloxy-cyclopentane carboxylate compound of formula (I) can be obtained through conventional separation and purification processes, such as extraction, distillation, crystallization, recrystallization, thin-layer chromatography, or column chromatography.

Among the intermediates used in the synthesis of the compounds of the general formula (I), the following 2-hydrocarbyl-2-hydrocarbyloxycarbonyl-cyclopentanol compounds:

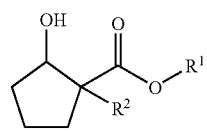

(II)

wherein $R^1$ is $C_1$-$C_4$alkyl; $R^2$ is selected from the group consisting of $C_1$-$C_{10}$alkyl, $C_3$-$C_{10}$cycloalkyl, $C_4$-$C_9$alkylcycloalkyl, $C_4$-$C_9$cycloalkylalkyl, $C_6$-$C_{10}$aryl, $C_7$-$C_{10}$alkaryl and $C_7$-$C_{10}$aralkyl, with the proviso that $R^2$ is not one of methyl, propyl and benzyl, are novel compounds synthesized by the inventors.

Such novel intermediates are, for example,
2-ethyl-2-ethoxycarbonyl-cyclopentanol;
2-n-butyl-2-ethoxycarbonyl-cyclopentanol;

2-n-hexyl-2-ethoxycarbonyl-cyclopentanol;
2-p-methylbenzyl-2-ethoxycarbonyl-cyclopentanol;
2-iso-butyl-2-ethoxycarbonyl-cyclopentanol;
2-n-pentyl-2-ethoxycarbonyl-cyclopentanol; and
2-iso-pentyl-2-ethoxycarbonyl-cyclopentanol.

The present invention is also directed to use of 1-hydrocarbyl-2-acyloxy-cyclopentane carboxylate compounds of the formula (I) in the preparation of catalysts for olefin polymerization, such as Ziegler-Natta type polypropylene catalysts. When used as electron donor in the preparation of Ziegler-Natta catalysts for olefin polymerization, 1-hydrocarbyl-2-acyloxy-cyclopentane carboxylate compounds of the formula (I) exhibit excellent performance in enhancing activity and stereospecificity of the catalysts in polymerization. Said compounds are particularly suitably used as internal electron donor in the preparation of spherical polypropylene catalyst.

EXAMPLES

Examples 1-12

Preparation of 1-hydrocarbyl-2-oxocyclopentane carboxylate by hydrocarbylating on α-carbon Example 1

Methyl 1-benzyl-2-oxocyclopentane carboxylate 29.0 grams of anhydrous potassium carbonate and 132 ml of acetone were mixed, then with stirring, to the resulting mixture was dropwise added a solution of 13.0 ml of methyl 2-oxocyclopentane carboxylate in 66 ml of acetone. After stirring at room temperature for 30 minutes, 13.7 ml of benzyl bromide was dropwise added thereto, and the reaction was allowed to continue under reflux for 6 hours. Then the reaction mixture was cooled to room temperature, filtered, and concentrated, and 150 ml of toluene was added thereto. The resulting solution was washed with water (3×150 ml), dried over anhydrous sodium sulfate, concentrated, and distilled under reduced pressure. 13.4 g of colorless liquid as a distillate cut of 161-162° C./4.8 mmHg was collected. Yield: 55.1%.

$^1$H NMR(400 MHz, CDCl$_3$): 1.60-2.44 (m, 6H, 3CH$_2$), 3.16 (dd, 2H, CH$_2$Ph, J=13.6 Hz), 3.72 (s, 3H, OCH$_3$), 7.11-7.14(m, 2H, ArH), 7.20-7.30(m, 3H, ArH).

Example 2

Ethyl 1-benzyl-2-oxocyclopentane carboxylate 38.7 grams of anhydrous potassium carbonate and 90 ml of acetone were mixed, then with stirring, to the resulting mixture was dropwise added a solution of 10.4 ml of ethyl 2-oxocyclopentane carboxylate in 45 ml of acetone. After stirring at room temperature for 35 minutes, 16.7 ml of benzyl bromide was dropwise added thereto, and the reaction was allowed to continue under reflux for 3 hours. Then the reaction mixture was cooled to room temperature, filtered, concentrated, and distilled under reduced pressure. 11.54 g of colorless liquid as the second distillate cut was collected. Yield: 66.9%.

$^1$H NMR(400 MHz, CDCl$_3$): 1.26 (t, 3H, CH$_3$, J=7.2 Hz), 1.50-2.50 (m, 6H, 3CH$_2$), 3.16 (dd, 2H, CH$_2$Ph, J=13.6 Hz), 4.18 (q, 2H, OCH$_2$, J=7.2 Hz), 7.11-7.30 (m, 5H, ArH).

Example 3

Ethyl 1-methyl-2-oxocyclopentane carboxylate

Under vigorously agitation, 20.3 g of ethyl 2-oxocyclopentane carboxylate was added to 53.8 g of fine powdery anhydrous potassium carbonate, and after stirring for several minutes, to the mixture was added 90 ml of acetone. The reaction mixture was further stirred for 15 to 30 minutes at room temperature, then to the mixture was dropwise added 36.9 g of methyl iodide. Upon the completion of the addition, the reaction mixture was heated for reflux for 1 hour. The solvent was removed under reduced pressure, and the solid residue was washed with diethyl ether. The washing liquor was collected and washed with water. After removing the solvent, 22.0 g of pale yellow liquid was obtained. The liquid was distilled under reduced pressure, and 20.9 g of colorless liquid as a distillate cut of 131-133° C./39 mmHg was collected. Yield: 94.6%.

$^1$H NMR(400 MHz, CDCl$_3$): 1.25 (t, 3H, CH$_2$CH$_3$), 1.31 (s, 3H, CH$_3$), 1.85-2.53 (m, 6H, 3CH$_2$), 4.16 (q, 2H, OCH$_2$).

Example 4

Preparation of ethyl 1-ethyl-2-oxocyclopentane carboxylate

Under vigorously agitation, 31.2 g (purity of 90%,) of ethyl 2-oxocyclopentane carboxylate was added to 76.04 g (purity of 98%) of ground anhydrous potassium carbonate, and after stirring for several minutes, to the mixture was added 100 ml of acetone. The reaction mixture was further stirred for about 15 minutes, then to the mixture was dropwise added 29.51 ml (purity of 98.5%) of ethyl iodide. Upon the completion of the addition, the reaction mixture was heated for reflux for 5 hours. The reaction mixture was filtered under the reduced pressure, and the filter cake was washed with diethyl ether until its color was purely white. Pale yellow filtrate was collected and dried over anhydrous magnesium sulfate, then the solvent was removed. The residue was distilled under reduced pressure, and 32.03 g of colorless liquid as a distillate cut of 130-134° C./18 mmHg was collected. Yield-96.7%. MS: m/e 184(M$^{+}$), 156(M$^{+}$"—C$_2$H$_5$), 140(M$^{+}$"—OCH$_2$CH$_3$), 139, 101(M$^{+}$"—CO$_2$CH$_2$CH$_3$), 127(155—CH$_2$CH$_2$), 111(156-OCH$_2$CH$_3$), 55(base).

IR (film,cm$^{-1}$): 2965(v$_{as}$CH$_3$), 2873, 1755(vC=O), 1724 (vO—C=O), 1225 (vC—O—C).

Example 5

Preparation of methyl 1-ethyl-2-oxocyclopentane carboxylate

Under vigorously agitation, 14.8 g of methyl 2-oxocyclopentane carboxylate was added to 41.9 g of fine powdery anhydrous potassium carbonate, and after stirring for several minutes, to the mixture was added 100 ml of acetone. The reaction mixture was further stirred for 15 to 30 minutes at room temperature, then thereto was dropwise added 31.2 g of ethyl iodide. Upon the completion of the addition, the reaction mixture was heated for reflux for 2 hours. The solvent was removed under reduced pressure, and solid residue was washed with diethyl ether. The washing liquor was collected and washed with water. After removing the solvent, 18.0 g of pale yellow liquid was obtained, The liquid was distilled under reduced pressure, and 15.9 g of colorless liquid as a distillate cut of 122-124° C./25 mmHg was collected. Yield: 93.5%.

$^1$H NMR(400 MHz, CDCl$_3$): 0.90 (t, J=7.5 Hz, 3H, CH$_2$CH$_3$), 1.61-2.40 (m, 8H, 4CH$_2$), 3.71 (s, 3H, OCH$_3$).

Example 6

Ethyl 1-n-butyl-2-oxocyclopentane carboxylate

Under vigorously agitation, 52.0 g (purity of 90%) of ethyl 2-oxocyclopentane carboxylate was added to 126.73 g (purity of 98%,) of ground anhydrous potassium carbonate, and after stirring for several minutes, to the mixture was added 100 ml of acetone. The reaction mixture was further stirred for about 15 minutes, then thereto was dropwise added 66.0 ml (purity of 98%,) of 1-bromo-n-butane. Upon the completion of the addition, the reaction mixture was heated for reflux for 5 hours. The reaction mixture was filtered under the reduced pressure, and the filter cake was washed with diethyl ether until its color was purely white. Pale yellow filtrate was collected and dried over anhydrous magnesium sulfate, then the solvent was removed. The residue was distilled under reduced pressure, and 53.39 g of colorless liquid as a distillate cut of 140-141° C./16 mmHg was collected. Yield: 83.9%. MS: m/e 212(M$^{+\cdot}$), 197(M$^{+\cdot}$—CH$_3$), 184(M$^{+\cdot}$—CH$_2$CH$_2$), 167(M$^{+\cdot}$—OCH$_2$CH$_3$), 156 (M$^{+\cdot}$—C$_4$H$_9$,base), 139(M$^{+\cdot}$—CO$_2$CH$_2$CH$_3$), 127, 111, 55.

$^1$H NMR(400 MHz, CDCl$_3$): 0.89(t, 3H, (CH$_2$)$_3$CH$_3$), 1.26(t, 3H, OCH$_2$CH$_3$) 1.23-2.54(m, 12H, 6CH$_2$), 4.16(q, 2H, OCH$_2$).

Example 7

Ethyl 1-iso-butyl-2-oxocyclopentane carboxylate

Under vigorously agitation, 13.9 g of ethyl 2-oxocyclopentane carboxylate was added to 33.4 g of fine powdery anhydrous potassium carbonate and 1.14 g of benzyl triethyl ammonium chloride. After stirring for several minutes, to the mixture was added 60 ml of N,N-dimethyl formamide and 21.9 g of iso-butyl bromide. Upon the completion of the addition, the reaction was heated to 55° C. and allowed to continue for 6 hours with stirring. The solvent was removed under reduced pressure, and solid residue was washed with diethyl ether. The washing liquor was collected and washed with water, and removing the solvent gave a crude product. The crude product was distilled under reduced pressure, and 15.3 g of colorless liquid as a distillate cut of 139-142° C./15 mmHg was colleted. Yield: 90.0%.

$^1$H NMR(600 MHz, CDCl$_3$): 0.89(q, J=6.9 Hz, 6H, CH(CH$_3$)$_2$), 1.42(q, J=6.9 Hz, 1H), 1.27 (t, J=6.9 Hz, 3H, OCH$_2$CH$_3$), 1.66-2.68 (m, 8H), 4.12-4.21(m, 2H, OCH$_2$CH$_3$).

Example 8

Ethyl 1-n-hexyl-2-oxocyclopentane carboxylate

Under vigorously agitation, 31.2 g of ethyl 2-oxocyclopentane carboxylate was added to 84.5 g purity of 98%) of ground anhydrous potassium carbonate, and after stirring for several minutes, to the mixture was added 100 ml Of acetone. The reaction mixture was further stirred for about 15 minutes, then thereto was dropwise added 57.54 ml (purity of 98%) of 1-bromo-n-hexane. Upon the completion of the addition, the reaction mixture was heated for reflux for 5 hours. The reaction mixture was filtered under the reduced pressure, and the filter cake was washed with diethyl ether until its color was purely white. Pale yellow filtrate was collected and dried over anhydrous magnesium sulfate, then the solvent was removed. The residue was distilled under reduced pressure, and 41.89 g of colorless liquid as a distillate cut of 156-160° C./23 mmHg was collected. Yield: 87.3%. MS: m/e 240(M$^{+\cdot}$), 212(M$^{+\cdot}$—CH$_2$CH$_2$), 195(M$^{+\cdot}$—OCH$_2$CH$_3$), 167(M$^{+\cdot}$—CO$_2$CH$_2$CH$_3$), 156(base), 155, 127, 111.

IR (film,cm$^{-1}$): 2955($v_{as}$CH$_3$), 2872, 1755(vC=O), 1722 (vO—C=O), 1223(vC—O—C).

Example 9

Ethyl 1-p-methylbenzyl-2-oxocyclopentane carboxylate

Under vigorously agitation, 39.0 g of ethyl 2-oxocyclopentane carboxylate was added to 105.6 g (purity of 98%) of ground anhydrous potassium carbonate, and after stirring for several minutes, to the mixture was added 100 ml of acetone. The reaction mixture was further stirred for about 15 minutes, then thereto was dropwise added 34.35 ml (purity of 98%) of p-methylbenzyl bromide. Upon the completion of the addition, the reaction mixture was heated for reflux for 4 hours. The reaction mixture was filtered under the reduced pressure, and the filter cake was washed with diethyl ether until its color was purely white. Pale yellow filtrate was collected and dried over anhydrous magnesium sulfate, then the solvent was removed. The residue was distilled under reduced pressure, and 53.57 g of colorless liquid as a distillate cut of 144-146° C./100 Pa was collected. Yield: 82.4%. MS: m/e 260(M$^{+\cdot}$), 242, 232(M$^{+\cdot}$—CH$_2$CH$_2$), 215 (M$^{+\cdot}$—OCH$_2$CH$_3$), 187(M$^{+\cdot}$—CO$_2$CH$_2$CH$_3$), 171, 155 (M$^{+\cdot}$—C$_8$H$_9$) 127, 105(base), 77.

IR (film,cm$^{-1}$): 2978, 1745, 1724, 1629, 1576, 1264.

$^1$HNMR(400 MHz,CDCl$_3$): 1.25(t, 3H, OCH$_2$CH$_3$), 1.61-2.04(m, 6H, 3CH$_2$), 2.29 (s, 3H, CH$_2$C$_6$H$_5$CH$_3$), 3.10(q, 2H, CH$_2$C$_6$H$_5$CH$_3$), 4.17(q, 2H, CO$_2$CH$_2$CH$_3$), 7.00-7.28(m, 5H, —CH$_2$C$_6$H$_5$CH$_3$).

Example 10

Ethyl 1-n-propyl-2-oxocyclopentane carboxylate

The target alkylated product as a distillate cut of 138-142° C./18 mmHg was obtained following the procedure as described in Example 4, except that n-propyl iodide was used to replace ethyl iodide as haloalkane agent. MS: m/e 199(M$^{+\cdot}$+1), 170(M$^{+\cdot}$—C$_2$H$_5$), 156(M$^{+\cdot}$—OCH$_2$CH$_3$, base), 141, 115(M$^{+\cdot}$—CO$_2$CH$_2$CH$_3$), 110, 97, 82, 67, 55

IR (film, cm$^{-1}$): 2961($v_{as}$CH$_3$), 2875($v_{as}$CH$_2$), 1755 ($v_{as}$C=O), 1722(vO—C=O), 1679, 1626, 1226($v_{as}$C—O—C).

$^1$HNMR(600 MHz, CDCl$_3$): 0.90(t, 3H, CH$_2$CH$_2$CH$_3$), 1.26(t, 3H,CO$_2$CH$_2$CH$_3$), 1.87-2.62 (m, 10H, 5CH$_2$), 4.17 (q, 2H, CO$_2$CH$_2$CH$_3$).

Example 11

Ethyl 1-n-pentyl-2-oxocyclopentane carboxylate

Under mechanical agitation, 31.20 g (purity of 90%) of ethyl 2-oxocyclopentane carboxylate was added to 76.04 g (purity of 98%) of ground anhydrous potassium carbonate, and after stirring for several minutes, to the mixture was added 100 ml of acetone. The reaction mixture was further stirred for about 15 minutes, then thereto was dropwise added 45.86 ml (purity of 98% of 1-bromo-n-pentane. Upon the completion of the addition, the reaction mixture was heated for reflux for 6 hours. The reaction mixture was filtered under the reduced pressure, and the filter cake was washed with diethyl ether until its color was purely white. Pale yellow filtrate was collected and dried over anhydrous magnesium sulfate, then the solvent was removed. The residue was distilled under reduced pressure, and 36.42 g of colorless liquid as a distillate cut of 156-162° C./22 mmHg was collected. Yield: 89.52%. MS: m/e 227($M^+$"+1), 226 ($M^+$"), 198, 181, 169, 156, 141, 127, 110, 95.

Example 12

Ethyl 1-iso-pentyl-2-oxocyclopentane carboxylate

Under vigorous agitation, 34.67 g (purity of 90%) of ethyl 2-oxocyclopentane carboxylate was added to 112.65 g (purity of 98%,) of ground anhydrous potassium carbonate, and after stirring for several minutes, to the mixture was added 100 ml of acetone. The reaction mixture was further stirred for about 15 minutes, then thereto was dropwise added 51.36 ml (purity of 98%) of 1-bromo-iso-pentane. Upon the completion of the addition, the reaction mixture was heated for reflux for 6 hours. The reaction mixture was filtered under the reduced pressure, and the filter cake was washed with diethyl ether until its color was purely white. Pale yellow filtrate was collected and dried over anhydrous magnesium sulfate, then the solvent was removed. The residue was distilled under reduced pressure, and 32.80 g of colorless liquid as a distillate cut of 142-147° C./15 mmHg was collected. Yield: 72.60%. MS: m/e 227($M^{30}$ +1), 226 ($M^+$), 211 ($M^+$—$CH_3$) 198($M^+$—$CH_2CH_2$) 171 ($M^+$—$OCH_2CH_3$), 156 ($M^+$—$C_5H_{11}$, base), 153($M^+$—$CO_2$$CH_2CH_3$), 127(155-$CH_2CH_2$), 111(156-$OCH_2CH_3$), 55.

IR (film, $cm^{-1}$): 2957($v_{as}CH_3$), 2871($v_{as}CH_2$), 1752 ($v_{as}C=O$), 1721($v_{as}O-C=O$), 1222($v_{as}C-O-C$).

Example 13-22

Preparation of 2-hydrocarbyl-2-hydrocarbyloxycarbonyl-cyclopentanol intermediate (also known as 1-hydrocarbyl-2-hydroxy-cyclopentane carboxylate) by reduction reaction

Example 13

2-benzyl-2-methoxycarbonyl-cyclopentanol (or methyl 1-benzyl-2-hydroxy-cyclopentane carboxylate)

2.77 grams of methyl 1-benzyl-2-oxocyclopentane carboxylate obtained from Example 1 were dissolved in 120 ml of methanol, and to the solution was added 2.64 g of anhydrous calcium chloride. The reaction mixture was cooled to about 2° C. using an ice-salt bath, then 0.54 g of sodium borohydride was slowly and batchwise added with stirring, and additional 0.1 g of sodium borohydride was added to the mixture. The reaction mixture was stirred for further 30 minutes and concentrated then to give a white slurry. To the slurry were added 50 ml of methylene chloride and 50 ml of saturated aqueous solution of ammonium chloride. Organic layer was separated, washed with distilled water for three times, dried over anhydrous sodium sulfate, filtered and concentrated to give 2.40 g of pale yellow oil. MS: 234($M^+$").

$^1$H NMR(400 MHz, $CDCl_3$): 1.50-2.20 (m, 6H, 3$CH_2$), 2.25(d, 1H, CHOH), 2.77 & 3.25 (dd, 2H, $CH_2$Ph, J=13.6 Hz), 3.60 (s, 3H, $OCH_3$), 4.34 (m, 1H, CHOH), 7.00-7.16 (m, 2H, ArH), 7.16-7.40(m, 3H, ArH).

Example 14

2-benzyl-2-ethoxycarbonyl-cyclopentanol (or ethyl 1-benzyl-2-hydroxy-cyclopentane carboxylate)

With stirring, 16.2 g of fine powdery calcium chloride was batchwise added to 730 ml of methanol solution containing 18.0 g of ethyl 1-benzyl-2-oxocyclopentane carboxylate obtained in Example 2. The reaction mixture was stirred at room temperature for 30 minutes, and then cooled to 0° C. using an ice bath. Then 3.31 g of sodium borohydride was batchwise added, and the reaction was stirred for further 30 minutes. The reaction mixture was concentrated, and the residue was dissolved into methylene chloride and aqueous solution of ammonium chloride. The organic layer was washed with saline solution and dried over anhydrous sodium sulfate. Removing solvent gave 17.4 g of pale yellow liquid.

$^1$H NMR(300 MHz, $CDCl_3$): 1.17 & 1.23(2t, J=7.1 Hz, 3H, $OCH_2CH_3$), 1.68-2.04 (m, 6H, 3$CH_2$), 2.20 (d, 1H, CHOH), 2.79 & 3.26 (dd, J=13.6 Hz, 2H, $CH_2C_6H_5$), 4.07 (q, J=7.1 Hz, 2H, $OCH_2CH_3$), 4.33-4.38 (m, 1H, CHOH), 7.10-7.30 (m, 5H, $CH_2C_6H_5$).

This Example was also separately carried out as follows:

5.86 grams of ethyl 1-benzyl-2-oxocyclopentane carboxylate were dissolved in 240 ml of methanol, and to the solution was added 5.28 g of anhydrous calcium chloride. The reaction mixture was cooled to about 0° C. using an ice-salt bath, then 1.08 g of sodium borohydride was slowly and batchwise added with stirring, and additional 0.1 g of sodium borohydride was added to the mixture. The reaction mixture was stiffed for further 30 minutes and then concentrated to give a white slurry. To the slurry were added 100 ml of methylene chloride and 100 ml of saturated aqueous solution of ammonium chloride, Organic layer was separated, washed with distilled water for three times, dried over anhydrous sodium sulfate, filtered and concentrated to give 4.42 g of pale yellow oil. MS: 249($M^+$"+1), 248($M^+$"), 230($M^+$"—$CH_2CH_2$), 220($M^+$"–$H_2O$), 184, 174, 157($M^+$"—$CH_2C_6H_5$), 145, 129, 115, 91($^+CH_2C_6H_5$, base), 77.

IR (film,$cm^{-1}$): 3482(vOH), 1715(vO—C=O), 1187 (vC—O—C).

Example 15

2-ethyl-2-ethoxycarbonyl-cyclopentanol (or ethyl 1-ethyl-2-hydroxy-cyclopentane carboxylate)

27.6 grams of ethyl 1-ethyl-2-oxocyclopentane carboxylate obtained from Example 4 were weighed into a one-neck flask and then diluted using 60 ml of dry methanol. Then to the mixture was added 34.69 g of anhydrous calcium chloride, and the reaction mixture was stirred at room temperature for 30 minutes to give a clear solution. The temperature of reaction mixture was reduced to about 0° C. using an ice-salt bath, and 6.91 g of sodium borohydride was batchwise added. The reaction was stirred for 30 minutes, and then the solvent was removed. The residue was extracted using diethyl ether and water, then the organic phase was dried. Removing the solvent gave 25.19 g of colorless liquid.

MS: m/e 168($M^{+\cdot}-H_2O$), 158 ($M^{+\cdot}-CH_2CH_2$), 157($M^{+\cdot}-CH_2CH_3$), 141 ($M^{+\cdot}-OCH_2CH_3$), 129(base), 115, 113, 101.

IR (film,cm$^{-1}$): 3482($vOH$), 1726($vO-C=O$), 1221 ($vO-C=O$).

Example 16

2-n-butyl-2-ethoxycarbonyl-cyclopentanol (or ethyl 1-n-butyl-2-hydroxy-cyclopentane carboxylate)

8.48 grams of ethyl 1-n-butyl-2-oxocyclopentane carboxylate obtained from Example 6 were weighed into a one-neck flask and then diluted using 60 ml of dry methanol. Then to the mixture was added 9.25 g of anhydrous calcium chloride, and the reaction mixture was stirred at room temperature for 30 minutes to give a clear solution. The temperature of reaction mixture was reduced to about 0° C. using an ice-salt bath, and 1.824 g of sodium borohydride was batchwise added. The reaction was stirred for 30 minutes, and then the solvent was removed. The residue was extracted using diethyl ether and water, then the organic phase was dried. Removing the solvent gave 19.21 g of colorless liquid. MS: m/e 214($M^{+\cdot}$), 196(($M^{+\cdot}-H_2O$), 186 ($M^{+\cdot}-CH_2CH_2$), 169($M^{+\cdot}-OCH_2CH_3$), 157($M^{+\cdot}-CH_2CH_2CH_2CH_3$,base), 141($M^{+\cdot}-CO_2CH_2CH_3$), 125, 115.

IR (film,cm$^{-1}$): 3486($vOH$), 1724($vO-C=O$), 1222 ($vC-O-C$).

$^1$HNMR(400 MHz,CDCl$_3$): 0.89(t, 3H, $CH_2CH_2CH_2CH_3$), 1.26(t, 3H, $CO_2CH_2CH_3$), 1.27-2.12 (m, 13H, CHOH, 6CH$_2$), 4.18(q, 2H, $CO_2CH_2CH_3$), 4.28(t, 1H, —CHOH).

Example 17

2-n-hexyl-2-ethoxycarbonyl-cyclopentanol (or ethyl 1-n-hexyl-2-hydroxy-cyclopentane carboxylate)

14.4 grams of ethyl 1-n-hexyl-2-oxocyclopentane carboxylate obtained from Example 8 were weighed into a one-neck flask and then diluted using 60 ml of dry methanol. Then to the mixture was added 13.87 g of anhydrous calcium chloride, and the reaction mixture was stirred at room temperature for 30 minutes to give a clear solution. The temperature of reaction mixture was reduced to about 0° C. using an ice-salt bath, and 2.76 g of sodium borohydride was batchwise added. The reaction was stirred for 30 minutes, and then the solvent was removed. The residue was extracted using diethyl ether and water, then the organic phase was dried. Removing the solvent gave 13.42 g of colorless liquid. MS: m/e 242($M^{+\cdot}$), 224(($M^{+\cdot}-H_2O$), 214 ($M^{+\cdot}-CH_2CH_2$), 197($M^{+\cdot}-OCH_2CH_3$), 185(214-$CH_2CH_3$), 169($M^{+\cdot}-CO_2CH_2CH_3$), 157($M^{+\cdot}-(CH2)_5CH_3$, base), 127(155-$CH_2CH_2$), 125, 115.

IR (film,cm$^{-1}$): 3480($vOH$), 1728($vO-C=O$), 1224 ($vC-O-C$).

$^1$HNMR(400 MHz,CDCl$_3$): 0.88(t, 3H, $(CH_2)_5CH_3$), 1.25 (t, 3H, $CO_2CH_2H_3$), 1.27-2.32 (m, 17H, OH, 8CH$_2$), 4.18(q, 2H, $CO_2CH_2CH_3$), 4.28(t, 1H, CHOH).

Example 18

2-p-methylbenzyl-2-ethoxycarbonyl-cyclopentanol (or ethyl 1-p-methylbenzyl-2-hydroxy-cyclopentane carboxylate)

31.2 grams of ethyl 1-p-methylbenzyl-2-oxocyclopentane carboxylate obtained from Example 9 were weighed into a one-neck flask and then diluted using 60 ml of dry methanol. Then to the mixture was added 27.75 g of anhydrous calcium chloride, and the reaction mixture was stirred at room temperature for 30 minutes to give a clear solution. The temperature of reaction mixture was reduced to about 0° C. using an ice-salt bath, and 5.53 g of sodium borohydride was batchwise added, The reaction was stirred for 30 minutes, and then the solvent was removed. The residue was extracted using diethyl ether and water, then the organic phase was dried. Removing the solvent gave 29.56 g of colorless liquid. MS: m/e 262($M^{+\cdot}$), 244($M^{+\cdot}-CH_2CH_2$), 234($M^{+\cdot}-H_2O$), 216, 205, 198, 188, 171, 159, 157($M^{+\cdot}-CH_2C_6H_5$), 145, 143, 131, 129, 115, 105(base), 91, 77.

IR (film, cm$^{-1}$): 3470($vOH$), 1718($vO-C=O$), 1188 ($vC-O-C$).

$^1$HNMR(400 MHz,CDCl$_3$): 1.17 & 1.23(2t, 3H, —OCH$_2$CH$_3$), 1.68-2.06(m, 6H, 3CH$_2$,), 2.18(d, 1H, CHOH), 2.30(s, 3H, —C$_6$H$_5$CH$_3$), 2.75 & 3.20(2d, 2H, CH$_2$C$_6$H$_5$CH$_3$), 4.07(q, 2H, CO$_2$CH$_2$ CH$_3$), 4.33(t, 1H, CHOH), 6.98-7.12(m,4H, —CH$_2$C$_6$H$_4$CH$_3$).

Example 19

2-n-propyl-2-ethoxycarbonyl-cyclopentanol (or ethyl 1-n-propyl-2-hydroxy-cyclopentane carboxylate)

29.70 grams of ethyl 2-oxo-1-n-propyl-cyclopentane carboxylate were weighed into a one-neck flask and then diluted using 60 ml of dry methanol. Then to the mixture was added 34.69 g of anhydrous calcium chloride, and the reaction mixture was stirred at room temperature for 30 minutes to give a clear solution. The temperature of reaction mixture was reduced to about 0° C. using an ice-salt bath, and 6.91 g of sodium borohydride was batchwise added. The reaction was stirred for 30 minutes, and then the solvent was removed. The residue was extracted using diethyl ether and water, then the organic phase was dried. Removing the solvent gave 27.24 g of colorless liquid. MS: m/e 182($M^+$-H$_2$O), 172($M^+$—CH$_2$CH$_2$), 157($M^+$—CH$_2$CH$_2$CH$_3$), 143, 115(base), 101, 84, 55.

IR (film, cm$^{-1}$): 3476, 2961($v_{as}CH_3$), 2875($v_{as}CH_2$), 1725($v_{as}O-C=O$), 1619, 1220($v_{as}C-O-C$).

$^1$NMR(600 MHz, CDCl$_3$): 0.91(t, 3H, CH$_2$CH$_2$CH$_3$), 1.28(t, 3H, CO$_2$CH$_2$CH$_3$), 1.45-2.20 (m, 11H, CHOH, 5CH$_2$), 4.16(q, 2H, CO$_2$CH$_2$CH$_3$), 4.29(t, 1H, —CHOH).

Example 20

2-iso-butyl-2-ethoxycarbonyl-cyclopentanol (or ethyl 1-iso-butyl-2-hydroxy-cyclopentane carboxylate)

The target product as a colorless liquid was obtained according to the procedure as described in Example 16 except that ethyl 1-iso-butyl-2-oxocyclopentane carboxylate obtained in Example 7 was used to replace ethyl 1-n-butyl-2-oxocyclopentane carboxylate. MS: m/e 196($M^+$-H$_2$O), 186 ($M^+$—CH$_2$CH$_2$), 171($M^+$—CH(CH$_3$)$_2$), 157 ($M^+$—CH$_2$CH(CH$_3$)$_2$), 143, 129, 125(base).

IR (film, cm$^{-1}$): 3485($vOH$), 1726($vO-C=O$), 1218 ($vC-O-C$).

$^1$HNMR(600 MHz,CDCl$_3$): 0.84&0.90(d, 6H, CH (CH$_3$)$_2$), 1.25(t, 3H, OCH$_2$CH$_3$), 1.46-2.18(m, 10H, OH, 3CH$_2$, CH$_2$CH(CH$_3$)$_2$), 4.12(q, 2H, CO$_2$CH$_2$CH$_3$), 4.23(t, 1H, CHOH)

Example 21

2-n-pentyl-2-ethoxycarbonyl-cyclopentanol (or ethyl 1-n-pentyl-2-hydroxy-cyclopentane carboxylate)

36.00 grams of ethyl 2-oxo-1-n-pentyl-cyclopentane carboxylate were weighed into a one-neck flask and then diluted using 60 ml of dry methanol. Then to the mixture was added 37.00 g of anhydrous calcium chloride, and the reaction mixture was stirred at room temperature for 30 minutes to give a clear solution. The temperature of reaction mixture was reduced to about 0° C. using an ice-salt bath, and 7.45 g of sodium borohydride was batchwise added. The reaction was stirred for 30 minutes, and then the solvent was removed. The residue was extracted using diethyl ether and water, then the organic phase was dried. Removing the solvent gave 36.05 g of colorless liquid. MS: m/e 228($M^+$), 227($M^{+'}$-1'), 210($M^+$-$H_2O$), 200($M^+$—$CH_2CH_2$), 183 ($M^+$—$OCH_2CH_3$), 171(base), 157($M^+$—$CH_2CH_2CH_2CH_3$), 125, 115.

Example 22

2-iso-pentyl-2-ethoxycarbonyl-cyclopentanol (or ethyl 1-iso-pentyl-2-hydroxy-cyclopentane carboxylate)

32.00 grams of ethyl 2-oxo-1-iso-pentyl-cyclopentane carboxylate were weighed into a one-neck flask and then diluted using 60 ml of dry methanol. Then to the mixture was added 32.74 g of anhydrous calcium chloride, and the reaction mixture was stirred at room temperature for 30 minutes to give a clear solution. The temperature of reaction mixture was reduced to about 0° C. using an ice-salt bath, and 7.85 g of sodium borohydride was batchwise added. The reaction was stirred for 30 minutes, and then the solvent was removed. The residue was extracted using diethyl ether and water, then the organic phase was dried. Removing the solvent gave 29.52 g of colorless liquid. MS: m/e 228($M^{+''}$), 227($M^{+'}$-1'), 200, 183, 171, 157, 155, 143, 125, 111, 101, 95, 87, 41(base).

IR (film,$cm^{-1}$): 3495(vOH), 1720(vO—C=O), 1210 (vC—O—C).

$^1$HNMR(400 MHz,$CDCl_3$): 0.87&0.89(d, 6H, CH$(CH_3)_2$), 110-2.14(m, 15H, OH, $OCH_2CH_3$, $5CH_2$, CHCH$(CH_3)_2$), 4.16(q, 2H, $CO_2CH_2CH_3$), 4.28(t, 1H, CHOH).

Examples 23-49

Preparation of 1-hydrocarbyl-2-acyloxy-cyclopentane carboxylate compounds via acylation

Example 23

Ethyl 1-benzyl-2-benzoyloxy-cyclopentane carboxylate 12.4 grams of 2-benzyl-2-ethoxycarbonyl-cyclopentanol obtained from Example 14 were diluted using 60 ml of methylene chloride. At room temperature and with magnetic stirring, 6.108 ml of pyridine was slowly added, then 8.876 ml of benzoyl chloride was dropwise added Upon the completion of the addition, the reaction was continued for 12 hours. Then solvent was removed, and the residue was extracted using ethyl acetate and water. Organic layer was washed, in turn, using 10% hydrochloric acid aqueous solution to pH of about 2, using saline solution to neutrality, and then using 10% aqueous solution of sodium carbonate for three times. The organic layer was dried, and removing solvent gave 19.71 g of yellow liquid. MS: m/e 353($M^+$+1), 352($M^+$), 351($M^+$-1), 279($M^+$—$CO_2CH_2CH_3$), 261($M^+$—$CH_2C_6H_5$), 247($M^+$—$C_6H_5CO$), 231($M^+$—$C_6H_5CO_2$), 201, 184, 156, 139, 105 (base), 91, 77.

$^1$HNMR(400 MHz,$CDCl_3$): 1.13 & 1.62(t, 3H, —$OCH_2CH_3$), 1.88-2.36(m, 6H, $3CH_2$), 2.99 & 3.02, 3.31 and 3.35(2d, 2H, $CH_2C_6H_5$), 4.06(q, 2H, $OCH_2CH_3$), 5.68(t, 1H, —CHO), 7.07-7.26(m, 5H, —$CH_2C_6H_5$), 7.48-8.18(m, 5H, $C_6H_5CO$).

Example 24

Ethyl 1-benzyl-2-p-methylbenzoyloxy-cyclopentane carboxylate 7.44 grams of 2-benzyl-2-ethoxycarbonyl-cyclopentanol obtained in Example 14 were diluted with 60 ml of methylene chloride. At room temperature and with magnetic stirring, 3.66 ml of pyridine was slowly added, then 6.12 ml of 4-methyl benzoyl chloride was dropwise added. Upon the completion of the addition, the reaction was continued under reflux condition for 12 hours. Then the procedure as described in Example 23 was followed, to give 12.53 g of yellow liquid. MS: m/e 367($M^+$+1), 366($M^+$), 364($M^+$-2), 293($M^+$—$CO_2CH_2CH_3$), 247($M^+$—$CH_3C_6H_4CO$), 231 ($M^+$—$CH_3C_6H_4CO_2$), 201, 184, 156, 139, 119 (base), 91, 77.

IR (film, $cm^{-1}$): 3042, 2977($v_{as}CH_3$), 2878, 1725(vO—C=O), 1273&1256(vC—O—C).

Example 25

Ethyl 1-benzyl-2-m-methylbenzoyloxy-cyclopentane carboxylate 12.79 grams of target product as a yellow liquid were obtained following the procedure as described in Example 24 except that 6.01 ml of 3-methyl-benzoyl chloride was used to replace 4-methyl-benzoyl chloride. MS: m/e 367 ($M^+$+1), 366($M^+$), 293($M^+$—$CO_2CH_2CH_3$), 247($M^+$—$CH_3C_6H_4CO$), 231$M^+$—$CH_3C_6H_4CO_2$), 201, 184, 156, 139, 119(base), 91, 77.

$^1$HNMR(400 MHZ,$CDCl_3$): 1.14(t, 3H, $OCH_2CH_3$), 1.75-2.37(m, 6H, $3CH_2$), 2.68(s, 3H, m-$CH_3C_6H_4CO$), 2.96&2.99, 3.30&3.33(dd, 2H, $CH_2C_6H_5$), 4.07 (q, 2H, $OCH_2CH_3$), 5.69(t, 1H, CHO), 7.08-7.30(m, 5H, $CH_2C_6H_5$), 7.41-7.97(m, 4H, m-C—$H_3C_6H_4CO$).

Example 26

Ethyl 1-benzyl-2-o-methylbenzoyloxy-cyclopentane carboxylate 12.08 grams of target product as a yellow liquid were obtained following the procedure as described in Example 24 except that 5.995 ml (0.045 mol) of 2-methyl-benzoyl chloride was used to replace 4-methyl-benzoyl chloride. MS: m/e 367($M^+$+1), 366($M^+$), 293($M^+$—$CO_2CH_2CH_3$), 247($M^+$—$CH_3C_6H_4CO$), 231($M^+$-$CH_3C_6H_4CO_2$), 201, 184, 156, 139, 119(base), 91, 77.

$^1$HNMR(400 MHz,$CDCl_3$); 1.15(t, 3H, $OCH_2CH_3$), 1.71-2.37(m, 6H, $3CH_2$), 2.65(s, 3H, o-$CH_3C_6H_4CO$, 2.94& 2.98, 3.29&3.33(dd, 2H, $CH_2C_6H_5$), 4.06 (q, 2H,$OCH_2CH_3$), 5.68(t, 1H, CHO), 7.06-7.29(m, 5H, $CH_2C_6H_5$), 7.40-7.97 (m, 4H, o-$CH_3C_6H_4CO$).

Example 27

Methyl 1-p-methylbenzyl-2-benzoyloxy-cyclopentane carboxylate 5.24 grams of 2-p-methylbenzyl-2-ethoxycarbonyl-cyclopentanol obtained in Example 18 were diluted with 60 ml of methylene chloride. At room temperature and with magnetic stirring, 2.44 ml of pyridine was slowly added, then 3.55 ml of benzoyl chloride was dropwise added. Upon the completion of the addition, the reaction was continued under reflux condition for 12 hours. Then the procedure as described in Example 23 was followed, to give 7.41 g of yellow liquid. MS: m/e 367($M^+$+1), 366($M^+$), 293($M^+$—$CO_2CH_2CH_3$), 261($M^+$—$C_6H_5CO_2$), 216, 198, 170, 155, 105, 91, 77.

$^1$HNMR(400 MHz,$CDCl_3$): 1.13(t, 3H, $OCH_2CH_3$), 1.73-2.12(m, 6H, $3CH_2$), 2.29(s, 3H, p-$CH_3C_6H_4CH$-$_2$), 2.94& 2.99, 3.27 &3.31(dd,2H, p-$CH_3C_6H_4CH_2$), 4.06 (q, 2H, $OCH_2CH_3$), 5.67(t, 1H, CHO), 6.94-7.05(m, 4H, $CH_2C_6H_4CH_3$-p), 7.23-8.13(m, 5H, $C_6H_5CO$).

Example 28

Methyl 1-p-methylbenzyl-2-p-methylbenzoyloxy-cyclopentane carboxylate 8.41 grams of target product as a yellow liquid were obtained following the procedure as described in Example 27 except that 4.08 ml of 4-methyl-benzoyl chloride was used to replace benzoyl chloride. MS: m/e 380($M^{+\cdot}$), 307 ($M^+$—$CO_2CH_2CH_3$), 245($M^+$—$CH_3C_6H_4CO_2$), 216, 198, 171, 155, 119(base), 91, 77.

Example 29

Methyl 1-p-methylbenzyl-2-m-methylbenzoyloxy-cyclopentane carboxylate 8.46 grams of target product as a brown liquid were obtained following the procedure as described in Example 27 except that 4.00 ml of 3-methyl-benzoyl chloride was used to replace benzoyl chloride. MS: m/e 380($M^{+\cdot}$), 379 ($M^+$-1), 307($M^+$—$CO_2CH_2CH_3$), 245($M^+$—$CH_3C_6H_4CO_2$), 216, 198, 170, 155, 119(base), 91, 77.

Example 30

Methyl 1-p-methylbenzyl-2-o-methylbenzoyloxy-cyclopentane carboxylate 8.32 grams of target product as a brown liquid were obtained following the procedure as described in Example 27 except that 4.00 ml of 2-methyl-benzoyl chloride was used to replace benzoyl chloride. MS: m/e, 380($M^+$), 379 ($M^+$-1), 307($M^+$—$CO_2CH_2CH_3$), 245($M^+$—$CH_3C_6H_4CO_2$), 216, 198, 170,155, 119(base), 91, 77.

Example 31

Ethyl 1-n-butyl-2-benzoyloxy-cyclopentane carboxylate 10.7 grams of ethyl 1-n-butyl-2-hydroxy-cyclopentane carboxylate obtained in Example 16 were diluted with 60 ml of methylene chloride. At room temperature and with magnetic stirring, 6.108 ml of pyridine was slowly added, then 8.876 ml of benzoyl chloride was dropwise added. Upon the completion of the addition, the reaction was continued for 12 hours. Then the procedure as described in Example 23 was followed, to give 19.06 g of brown liquid. The brown liquid was purified through column chromatography to give a liquid with a purity, measured by GC, of 96.03%. Yield: 93.7%. MS: 318($M^+$), 273($M^+$—$OCH_2CH_3$), 261($M^+$—$CH_2CH_2CH_2CH_3$), 245($M^+$—$CO_2CH_2CH_3$), 213, 197 ($M^+$—$C_6H_5CO_2$), 105(base), 77.

$^1$HNMR(600 MHz,$CDCl_3$): 0.80(t, 3H, —$CH_2CH_2CH_2CH_3$), 1.21(t, 3H, $CO_2CH_2CH_3$), 1.24-2.36 (m, 12H, $6CH_2$), 4.16(q, 2H, —$CO_2CH_2CH_3$), 5.68(q, 1H, —CHO), 7.26-8.02 (m, 5H, $C_6H_5CO$).

Example 32

Ethyl 1-n-butyl-2-p-methylbenzoyloxy-cyclopentane carboxylate 6.42 grams of ethyl 1-n-butyl-2-hydroxy-cyclopentane carboxylate obtained in Example 16 were diluted with 60 ml of methylene chloride. At room temperature and with magnetic stirring, 3.66 ml of pyridine was slowly added, then 6.12 ml of 4-methyl-benzoyl chloride was dropwise added. Then the procedure as described in Example 23 was followed, to give 11.77 g of brown liquid. MS: m/e 332($M^{+\cdot}$), 287($M^+$—$OCH_2CH_3$), 213($M^+$—$CH_3C_6H_4CO$), 197($M^+$—$CH_3C_6H_4CO_2$), 119 (base), 91.

Example 33

Ethyl 1-n-hexyl-2-benzoyloxy-cyclopentane carboxylate 12.1 grams of ethyl 1-n-hexyl-2-hydroxy-cyclopentane carboxylate obtained in Example 17 were diluted with 60 ml of methylene chloride. At room temperature and with magnetic stirring, 6.108 ml of pyridine was slowly added, then 8.876 ml of benzoyl chloride was dropwise added. Then the procedure as described in Example 23 was followed, to give 18.16 g of yellow liquid. MS: 346($M^{+\cdot}$), 345($M^+$-1), 301 ($M^+$—$OCH_2CH_3$), 273($M^+$—$CO_2CH_2CH_3$), 262, 241 ($M^+$-$C_6H_5CO$), 225($M^+$—$C_6H_5CO_2$), 195, 185, 151, 140, 105 (base), 77.

$^1$HNMR(300 MHz, $CDCl_3$): 0.80(t, 3H, $(CH_2)_5CH_3$), 1.05-2.36(m, 16H, $8CH_2$), 4.17(q, 2H, $CO_2CH_2CH_3$), 5.70 (d, 1H, CHO), 7.26-8.04((m, 5H, $C_6H_5CO$).

Example 34

Ethyl 1-n-hexyl-2-p-methylbenzoyloxy-cyclopentane carboxylate 7.44 grams of ethyl 1-n-hexyl-2-hydroxy-cyclopentane carboxylate obtained in Example 17 were diluted with 60 ml of methylene chloride. At room temperature and with magnetic stirring, 3.66 ml of pyridine was slowly added, then 6.12 ml of 4-methyl-benzoyl chloride was dropwise added. Then the procedure as described in Example 23 was followed, to give 12.53 g of yellow liquid. MS: m/e 360($M^{+\cdot}$), 315($M^+$—$OCH_2CH_3$), 287($M^+$—$CO_2CH_2CH_3$), 276, 241 ($M^+$-$CH_3C_6H_4CO$), 225($M^+$—$CH_3C_6H_4CO_2$), 195, 185, 151, 140, 119 (base), 91, 77.

Example 35

Ethyl 1-n-hexyl-2-m-methylbenzoyloxy-cyclopentane carboxylate 6.05 grams (0.025 mol) of ethyl 1-n-hexyl-2-hydroxy-cyclopentane carboxylate obtained in Example 17 were diluted with 60 ml of methylene chloride. At room temperature and with magnetic stirring, 3.05 ml (0.0375 mol) of pyridine was slowly added, then 4.99 ml of 3-methyl-benzoyl chloride was dropwise added. Then the procedure as described in Example 23 was followed, to give 10.01 g of brown liquid. MS: m/e 361($M^+$+1), 360($M^{+\prime}$), 315($M^+$—$OCH_2CH_3$), 287($M^+$—$CO_2CH_2CH_3$), 276, 241($M^+$—$CH_3C_6H_4CO$), 225($M^+$—$CH_3C_6H_4CO_2$), 195, 151, 140, 119(base), 118, 91, 77.

Example 36

Ethyl 1-n-hexyl-2-o-methylbenzoyloxy-cyclopentane carboxylate 9.82 grams of target product as a brown liquid were obtained following the procedure as described in Example 35 except that 4.96 ml of 2-methyl-benzoyl chloride was used to replace 3-methylbenzoyl chloride. MS: m/e 362 ($M^+$+2), 360($M^{+\prime}$), 315($M^+$—$OCH_2CH_3$), 287($M^+$—$CO_2CH_2CH_3$), 276, 241($M^+$—$CH_3C_6H_4CO$), 225($M^+$—$CH_3C_6H_4CO_2$), 195, 185, 151, 140, 119(base), 91.

Example 37

Ethyl 1-ethyl-2-acetoxy-cyclopentane carboxylate 5.58 grams of ethyl 1-ethyl-2-hydroxy-cyclopentane carboxylate obtained in Example 15 was diluted with 50 ml of methylene chloride. To the solution were added several drops of concentrated sulfuric acid, then dropwise added 4.32 ml of acetic anhydride. The mixture was allowed to react under reflux condition for 2 hours. The reaction mixture was washed with 50 ml of ethyl acetate and 50 ml of water, and organic layer was separated. Then the organic layer was washed with 10% aqueous solution of sodium carbonate twice, then with saline solution to neutrality, and dried over anhydrous magnesium sulfate. Removing solvent gave 5.91 g of colorless liquid. Yield after chromatography purification: 83.20%. MS: m/e 228($M^{+\prime}$), 183($M^+$—$OCH_2CH_3$), 169 ($M^+$—$CH_3CO_2$), 158, 155, 140, 129, 113, 101.

Example 38

Ethyl 1-ethyl-2-benzoyloxy-cyclopentane carboxylate

Ethyl 2-hydroxy-1-ethyl-cyclopentane carboxylate (4.90 g) was diluted using 60 ml of methylene chloride. At room temperature and with magnetic stirring, pyridine (3.22 ml) was slowly added, then benzoyl chloride (4.68 ml) was dropwise added. Upon the completion of the addition, the reaction was continued for 12 hours; Then solvent was removed, and the residue was extracted using ethyl acetate and water. Organic layer was washed in turn using 10% hydrochloric acid aqueous solution to pH of about 2, using saline solution to neutrality, using 10% aqueous solution of sodium carbonate for three times, and then using saline solution to neutrality. The organic layer was dried, and removing solvent gave 8.86 g of yellow liquid. MS: m/e 290($M^{+\prime\prime}$), 261, 216, 185, 168, 139, 105(base), 77.
$^1$HNMR(400 MHz,CDCl$_3$): 0.89(t, 3H, $CH_2CH_3$), 1.26(t, 3H, $CO_2CH_2CH_3$), 1.72-2.36(m, 8H, 4$CH_2$), 4.17(q, 2H, $CO_2CH_2CH_3$), 5.71(d, 1H, CHO), 7.26-8.04 (m, 5H, $C_6H_5CO$)

Example 39

Ethyl 1-ethyl-2-o-methylbenzoyloxy-cyclopentane carboxylate

Ethyl 2-hydroxy-1-ethyl-cyclopentane carboxylate (4.90 g) was diluted using 60 ml of methylene chloride. At room temperature and with magnetic stirring, pyridine (3.22 ml) was slowly added, then 2-methyl-benzoyl chloride (5.28 ml) was dropwise added. Upon the completion of the addition, the reaction was continued for 12 hours. Then solvent was removed, and the residue was extracted using ethyl acetate and water. Organic layer was washed, in turn, using 10% hydrochloric acid aqueous solution to pH of about 2, using saline solution to neutrality, using 10% aqueous solution of sodium carbonate for three times, and then using saline solution to neutrality. The organic layer was dried, and removing solvent gave 8.99 g of yellow liquid. MS: m/e 304($M^{+\prime\prime}$), 261, 244, 139, 119(base), 91.
$^1$HNMR(400 MHz,CDCl$_3$): 0.85(t, 3H, $CH_2CH_3$), 1.27(t, 3H, $CO_2CH_2CH_3$), 1.71-2.12(m, 8H, 4$CH_2$), 2.36 (s, 3H, o-$CH_3C_6H_4CO$), 4.18 (q, 2H, $CO_2CH_2CH_3$), 5.70(d, 1H, CHO), 7.26-7.83(m, 4H, o-$CH_3CH_4CO$)

Example 40

Ethyl 1-n-propyl-2-benzoyloxy-cyclopentane carboxylate

Ethyl 2-hydroxy-1-n-propyl-cyclopentane carboxylate (6.00 g) was diluted using 60 ml of methylene chloride. At room temperature and with magnetic stirring, pyridine (3.67 ml) was slowly added, then benzoyl chloride (5.33 ml, 0.045 mol) was dropwise added. Upon the completion of the addition, the reaction was continued for 12 hours. Then solvent was removed, and the residue was extracted using ethyl acetate and water. Organic layer was washed, in turn, using 10% hydrochloric acid aqueous solution to pH of about 2, using saline solution to neutrality, using 10% aqueous solution of sodium carbonate for three times, and then using saline solution to neutrality. The organic layer was dried, and removing solvent gave 10.00 g of yellow liquid, MS: m/e 305($M^{+\prime\prime}$+1), 304($M^+$), 259, 230, 199, 182, 153, 105(base), 77.
$^1$HNMR(400 MHz,CDCl$_3$): 0.83(t, 3H, $CH_2CH_2CH_3$), 1.26(t, 3H, $CO_2CH_2CH_3$), 166-2.37(m, 10H, 5$CH_2$), 4.16(q, 2H, $CO_2CH_2CH_3$), 5.71(d, 1H, CHO), 7.27-8.04 (m, 5H, $C_6H_5CO$).

Example 41

Ethyl 1-n-propyl-2-o-methylbenzoyloxy-cyclopentane carboxylate

Ethyl 2-hydroxy-1-n-propyl-cyclopentane carboxylate (6.00 g) was diluted using 60 ml of methylene chloride. At room temperature and with magnetic stirring, pyridine (3.66 ml) was slowly added, then 2-methyl-benzoyl chloride (5.95 ml) was dropwise added. Upon the completion of the addition, the reaction was continued for 12 hours. Then solvent was removed, and the residue was extracted using ethyl acetate and water. Organic layer was washed, in turn, using 10% hydrochloric acid aqueous solution to pH of about 2, using saline solution to neutrality, using 10% aqueous solution of sodium carbonate for three times, and then using saline solution to neutrality. The organic layer was dried, and removing solvent gave 9.61 g of yellow liquid. MS: m/e 319($M^{+\cdot}$+1), 318($M^{+\cdot}$), 273, 259, 199, 183, 153, 119(base), 91, 77.

$^1$HNMR(400 MHz,CDCl$_3$): 0.86(t, 3H, CH$_2$CH$_2$CH$_3$), 1.26(t, 3H, CO$_2$CH$_2$CH$_3$), 1.60-2.36(m, 10H, 5CH$_2$), 2.61 (s, 3H, o-CH$_3$C$_6$H$_4$CO), 4.17(q, 2H, CO$_2$CH$_2$CH$_3$), 5.70(q, 1H, CHO), 7.23-7.89 (m, 4H, o-CH$_3$C$_6$H$_4$CO).

Example 42

Ethyl 1-n-propyl-2-m-methylbenzoyloxy-cyclopentane carboxylate

Ethyl 2-hydroxy-1-n-propyl-cyclopentane carboxylate (6.00 g) was diluted using 60 ml of methylene chloride. At room temperature and with magnetic stirring, pyridine (3.66 ml) was slowly added, then 3-methyl-benzoyl chloride (6.00 ml) was dropwise added, Upon the completion of the addition, the reaction was continued for 12 hours. Then solvent was removed, and the residue was extracted using ethyl acetate and water. Organic layer was washed, in turn, using 10% hydrochloric acid aqueous solution to pH of about 2, using saline solution to neutrality, using 10% aqueous solution of sodium carbonate for three times, and then using saline solution to neutrality. The organic layer was dried, and removing solvent gave 10.05 g of yellow liquid. MS: m/e 319($M^+$+1), 318($M^{+\cdot\cdot}$), 273, 259, 244, 226, 199, 182, 119(base), 91, 77.

$^1$HNMR(400 MHz,CDCl$_3$): 0.85(t, 3H, CH$_2$CH$_2$CH$_3$), 1.26(t, 3H, CO$_2$CH$_2$CH$_3$), 1.65-2.33(m, 10H, 5CH$_2$), 2.41 (s, 3H, m-CH$_3$C$_6$H$_4$CO), 4.17 (q, 2H, CO$_2$CH$_2$CH$_3$), 5.70(q, 1H, CHO), 7.26-7.83(m, 4H, m-CH$_3$C$_6$H$_4$CO).

Example 43

Ethyl 1-n-propyl-2-p-methylbenzoyloxy-cyclopentane carboxylate

Ethyl 2-hydroxy-1-n-propyl-cyclopentane carboxylate (6.00 g) was diluted using 60 ml of methylene chloride. At room temperature and with magnetic stirring, pyridine (3.66 ml) was slowly added, then 4-methyl-benzoyl chloride (6.12 ml) was dropwise added. Upon the completion of the addition, the reaction was continued for 12 hours. Then solvent was removed, and the residue was extracted using ethyl acetate and water. Organic layer was washed, in turn, using 10% hydrochloric acid aqueous solution to pH of about 2, using saline solution to neutrality, using 10% aqueous solution of sodium carbonate for three times, and then using saline solution to neutrality. The organic layer was dried, and removing solvent gave 10.41 g of yellow liquid. MS: m/e 319($M^{+\cdot}$+1), 318($M^{+\cdot}$), 317($M^{+\cdot}$-1), 259, 230, 199, 182, 153, 105(base), 77.

$^1$HNMR(400 MHz,CDCl$_3$): 0.84(t, 3H, CH$_2$CH$_2$CH$_3$), 1.23(t, 3H, CO$_2$CH$_2$CH$_3$), 1.64-2.36(m, 10H, 5CH$_2$), 2.41(s, 3H, p-CH$_3$C$_6$H$_4$CO), 4.16(q, 2H, CO$_2$CH$_2$CH$_3$), 5.69(q, 1H, CHO), 7.23-7.93(m, 4H, p-CH$_3$C$_6$H$_4$CO).

Example 44

Ethyl 1-n-butyl-2-m-methylbenzoyloxy-cyclopentane carboxylate

Ethyl 2-hydroxy-1-n-butyl-cyclopentane carboxylate (6.42 g) was diluted using 60 ml of methylene chloride. At room temperature and with magnetic stirring, pyridine (3.66 ml) was slowly added, then 3-methyl-benzoyl chloride (6.00 ml) was dropwise added. Upon the completion of the addition, the reaction was continued for 12 hours. Then solvent was removed, and the residue was extracted using ethyl acetate and water. Organic layer was washed, in turn, using 10% hydrochloric acid aqueous solution to pH of about 2, using saline solution to neutrality, and then using 10% aqueous solution of sodium carbonate for three times, then using saline solution to neutrality. The organic layer was dried, and removing solvent gave 11.99 g of brown liquid. MS: m/e 332($M^{+\cdot}$), 287, 213, 196, 167, 119(base), 99.

$^1$HNMR(400 MHz,CDCl$_3$): 0.82(t, 3H, CH$_2$CH$_2$CH$_2$CH$_3$), 1.26(t, 3H, CO$_2$CH$_2$CH$_3$), 1.72-2.11 (m, 12H, 6CH$_2$), 2.41 (s, 3H, m-CH$_3$C$_6$H$_4$CO), 4.17(q, 2H, CO$_2$CH$_2$CH$_3$), 5.69 (q, 1H, CHO), 7.26-7.83(m, 4H, m-CH$_3$C$_6$H$_4$CO).

Example 45

Ethyl 1-n-butyl-2-o-methylbenzoyloxy-cyclopentane carboxylate

The target product as a yellow liquid was obtained according to the procedure as described in Example 44 except that 2-methylbenzoyl chloride was used to replace 3-methylbenzoyl chloride. MS: m/e 332($M^+$), 287($M^+$—OCH$_2$CH$_3$), 286, 213($M^+$—CH$_3$C$_6$H$_4$CO), 197($M^+$—CH$_3$C$_6$H$_4$CO$_2$), 119 (base), 91.

$^1$HNMR(400 MHz,CDCl$_3$): 0.83(t, 3H, CH$_2$CH$_2$CH$_2$CH$_3$), 1.26(t, 3H, CO$_2$CH$_2$CH$_3$), 1.66-2.36(m, 12H, 6CH$_2$), 2.61 (s, 3H, o-CH$_3$C$_6$H$_4$CO), 4.17 (q, 2H CO$_2$CH$_2$CH$_3$), 5.70(q, 1H, —CHO), 7.25-7.89 (m, 4H, o-CH$_3$C$_6$H$_4$CO).

Example 46

Ethyl 1-iso-butyl-2-benzoyloxy-cyclopentane carboxylate

Ethyl 2-hydroxy-1-iso-butyl-cyclopentane carboxylate (5.00 g) was diluted using 60 ml of methylene chloride. At room temperature and with magnetic stirring, pyridine (2.85 ml) was slowly added, then benzoyl chloride (4.15 ml,) was dropwise added. Upon the completion of the addition, the reaction was continued for 12 hours. Then solvent was removed, and the residue was extracted using ethyl acetate and water. Organic layer was washed, in turn, using 10% hydrochloric acid aqueous solution to pH of about 2, using saline solution to neutrality, using 10% aqueous solution of sodium carbonate for three times, and then using saline solution to neutrality. The organic layer was dried, and removing solvent gave 7.70 g of brown liquid. MS: m/e 319($M^{+\cdot}$+1), 318($M^{+\cdot}$), 273, 244, 213, 196, 105(base), 77.

$^1$HNMR(400 MHz,CDCl$_3$): 0.78&0.93(d, 6H, CH$_2$CH(CH$_3$)$_2$), 1.27(t, 3H, CO$_2$CH$_2$CH$_3$), 1.55-2.41(m, 9H,

CH(CH$_3$)$_2$, 4CH$_2$), 4.17(q, 2H, CO$_2$CH$_2$CH$_3$), 5.71(d, 1H, CHO), 7.26-8.04(m, 5H, C$_6$H$_5$CO).

Example 47

Ethyl 1-iso-butyl-2-o-methylbenzoyloxy-cyclopentane carboxylate

Ethyl 2-hydroxy-1-iso-butyl-cyclopentane carboxylate (5.00 g) was diluted using 60 ml of methylene chloride. At room temperature and with magnetic stirring, pyridine (2.85 ml) was slowly added, then 2-methyl-benzoyl chloride (4.64 ml) was dropwise added. Upon the completion of the addition, the reaction was continued for 12 hours. Then solvent was removed, and the residue was extracted using ethyl acetate and water. Organic layer was washed, in turn, using 10% hydrochloric acid aqueous solution to pH of about 2, using saline solution to neutrality, using 10% aqueous solution of sodium carbonate for three times, and then using saline solution to neutrality. The organic layer was dried, and removing solvent gave 9.47 g of brown liquid. MS: m/e 333(M$^+$+1), 332(M$^+$), 287(M$^+$—OCH$_2$CH$_3$), 197(M$^+$—CH$_3$C$_6$H$_4$CO$_2$), 119(base), 91, 77.

$^1$HNMR(400 MHz,CDCl$_3$): 0.81&0.87(d, 6H, CH$_2$CH(CH$_3$)$_2$), 1.28(t, 3H, CO$_2$CH$_2$CH$_3$), 1.53-2.38(m, 9H, CH(CH$_3$)$_2$, 4CH$_2$), 2.41 (s,3H, o-CH$_3$C$_6$H$_4$CO), 4.16(q,2H, —CO$_2$CH$_2$CH$_3$), 5.70(d, 1H, CHO), 7.23-7.90(m, 4H, o-CH$_3$C$_6$H$_4$CO).

Example 48

Ethyl 1-iso-butyl-2-m-methylbenzoyloxy-cyclopentane carboxylate

Ethyl 2-hydroxy-1-iso-butyl-cyclopentane carboxylate (5.00 g) was diluted using 60 ml of methylene chloride. At room temperature and with magnetic stirring, pyridine (2.85 ml) was slowly added, then 3-methyl-benzoyl chloride (4.68 ml) was dropwise added. Upon the completion of the addition, the reaction was continued for 12 hours. Then solvent was removed, and the residue was extracted using ethyl acetate and water. Organic layer was washed, in turn, using 10% hydrochloric acid aqueous solution to pH of about 2, using saline solution to neutrality, using 10% aqueous solution of sodium carbonate for three times, and then using saline solution to neutrality. The organic layer was dried, and removing solvent gave 7.77 g of yellow liquid. MS: m/e 333(M$^+$+1), 332(M$^+$), 287(M$^+$—OCH$_2$CH$_3$), 258, 213(M$^+$–CH$_3$C$_6$H$_4$CO), 197(M$^+$—CH$_3$C$_6$H$_4$CO$_2$), 119(base), 91, 77.

$^1$HNMR(400 MHz,CDCl$_3$): 0.78&0.92(d, 6H, CH$_2$CH(CH$_3$)$_2$), 1.26(t, 3H, CO$_2$CH$_2$CH$_3$), 1.57-1.89(m, 9H, CH(CH$_3$)$_2$, 4CH$_2$), 2.41(s, 3H, m-CH$_3$C$_6$H$_4$CO), 4.16(q,2H, CO$_2$CH$_2$CH$_3$), 5.69(d, 1H, CHO), 7.24-7.93(m, 4H, m-CH$_3$C$_6$H$_4$CO).

Example 49

Ethyl 1-iso-pentyl-2-benzoyloxy-cyclopentane carboxylate

Ethyl 2-hydroxy-1-iso-pentyl-cyclopentane carboxylate (6.84 g) was diluted using 60 ml of methylene chloride. At room temperature and with magnetic stirring, pyridine (3.66 ml) was slowly added, then benzoyl chloride (5.33 ml) was dropwise added. Upon the completion of the addition, the reaction was continued for 12 hours. Then solvent was removed, and the residue was extracted using ethyl acetate and water. Organic layer was washed, in turn, using 10% hydrochloric acid aqueous solution to pH of about 2, using saline solution to neutrality, using 10% aqueous solution of sodium carbonate for three times, and then using saline solution to neutrality. The organic layer was dried, and removing solvent gave 11.73 g of brown liquid. MS: m/e 332(M$^+$), 287(M$^+$—OCH$_2$CH$_3$), 259(M$^+$—CO$_2$CH$_2$CH$_3$), 227(M$^+$—C$_6$H$_5$CO), 211 (M$^+$—C$_6$H$_5$CO$_2$), 182, 171, 140, 105(base), 7

$^1$HNMR(400 MHz,CDCl$_3$): 0.77&0.89(d, 6H, CH$_2$CH$_2$CH(CH$_3$)$_2$), 1.27(t, 3H, CO$_2$CH$_2$CH$_3$), 1.58-2.36 (m, 11H, CH$_2$CH$_2$CH(CH$_3$)$_2$, 5CH$_2$), 4.17(q, 2H, CO$_2$CH$_2$CH$_3$), 5.70(d, 1H, CHO), 7.26-8.04(m, 5H, C$_6$H$_5$CO).

Unless otherwise indicated, the synthesis steps in each Example described above were carried out under atmosphere pressure; and the products in Example 13-49 were purified through chromatography before the spectroscopic analyses.

Examples 50-55

Preparation of Solid Catalyst Component and Propylene Polymerization

Preparation of Solid Catalyst Component:

7 grams of spherical MgCl$_2$.2.6C$_2$H$_5$OH particles having an average particle size of 50 μm (prepared according to the process as disclosed in Chinese Patent Application CN1330086A) were added into 80 ml of hexane to form a suspension. The suspension was cooled to −20° C., and a mixture of 20 ml of hexane and 20 ml of TiCl$_4$ was added thereto. Then the reaction mixture was warmed to 20° C. and maintained at that temperature for 30 minutes. The liquid was filtered off by suction, and then to the reactor were added 100 ml of TiCl$_4$ and 5.5 mmol of an electron donor compound according to the invention (see Table 1). The reaction mixture was heated to 100° C. and maintained at that temperature for 2 hours, then the liquid when hot was filtered off by suction. To the reactor was added additional 100 ml of TiCl$_4$. The reaction mixture was heated to 120° C. and maintained at that temperature for 2 hours, then the liquid when hot was filtered off by suction, The solids were washed with hexane at 50-60° C. for three times, and at room temperature for two times, with the amount of hexane used being 60 ml for each time. Then the spherical solids were dried at 40° C. under vacuum for 2 hours, to give a spherical solid catalyst component. Example 50-55 and electron donor compound used therein were shown in Table 1.

Propylene Polymerization:

At room temperature and under nitrogen flow, to a 5 L autoclave, which had been purged with nitrogen flow at 70° C. for 1 hour, were added 5 ml of solution of AlEt$_3$ in hexane (the concentration of AlEt$_3$ was 0.5 mmol/ml), 1 ml of solution of cyclohexyl methyl dimethoxy silane (CHMMS) in hexane (the concentration of CHMMS was 0.1 mmol/ml), and 9 mg of the solid catalyst components prepared above in 10 ml of dry hexane. The autoclave was closed, and 1.5 L of hydrogen gas and 1.5 Kg of liquid propylene were then introduced. With stirring, the reactor was heated to 70° C. within 5 minutes, and the polymerization was performed at that temperature for 2 hours. After stopping the stirrer and removing unpolymerized propylene monomer, polymer was collected. The polymer was dried at 70° C. under vacuum for 2 hours, then weighed to calculate the activity per hour of the catalyst (AC). Isotacticity of the polymer (I.I) was measured by boiling n-heptane extraction method, and melt index of the polymer (M.I) was measured according to GB/T3682-2000 standard test. Polymerization results are shown in Table 1.

TABLE 1

| Example No. | Electron donor compound of the present invention | Activity of Catalyst kgPP/gCat · h | I.I wt % | M.I g/10 min |
|---|---|---|---|---|
| 50 | Ethyl 1-benzyl-2-p-methylbenzoyloxy-cyclopentane carboxylate | 30.0 | 97.6 | 2.1 |
| 51 | Ethyl 1-benzyl-2-m-methylbenzoyloxy-cyclopentane carboxylate | 29.5 | 97.0 | 5.2 |
| 52 | Ethyl 1-benzyl-2-o-methylbenzoyloxy-cyclopentane carboxylate | 36.7 | 95.6 | 5.4 |
| 53 | Methyl 1-p-methylbenzyl-2-benzoyloxy-cyclopentane carboxylate | 30.0 | 97.0 | 5.5 |
| 54 | Ethyl 1-n-butyl-2-benzoyloxy-cyclopentane carboxylate | 33.9 | 96.8 | 5.5 |
| 55 | Ethyl 1-n-hexyl-2-benzoyloxy-cyclopentane carboxylate | 15.6 | 93.7 | 9.7 |

It can be seen from the results shown in Table 1 that the cyclopentane carboxylate compounds of the formula (I) according to the invention are suitable for used, as internal electron donor, in the preparation of spherical catalyst for propylene polymerization, and the catalyst is excellent in performance.

What is claimed is:

1. A cyclopentane carboxylate compound having a general formula (I):

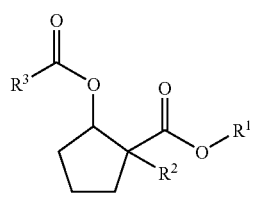

(I)

wherein
R$^1$, which can be identical or different from R$^2$ and R$^3$, selected from the group consisting of: linear or branched C$_1$-C$_{20}$ alkyl, C$_3$-C$_{20}$ cycloalkyl, C$_6$-C$_{20}$aryl, C$_7$-C$_{20}$alkaryl and C$_7$-C$_{20}$ aralkyl;
R$^2$, which can be identical or different from R$^1$ and R$^3$, is selected from the group consisting of: linear or branched C$_1$-C$_{20}$ alkyl, C$_3$-C$_{20}$ cycloalkyl, C$_6$-C$_{20}$aryl, C$_7$-C$_{20}$alkaryl and C$_7$-C$_{20}$ aralkyl; and
R$^3$, which can be identical or different from R$^1$ and R$^2$, is selected from the group consisting of: linear or branched C$_1$-C$_{20}$ alkyl, C$_3$-C$_{20}$ cycloalkyl, C$_6$-C$_{20}$aryl, C$_7$-C$_{20}$alkaryl and C$_7$-C$_{20}$ aralkyl.

2. The cyclopentane carboxylate compound according to claim 1, wherein:
R$^1$ is C$_1$-C$_8$ alkyl;
R$^2$ is selected from the group consisting of C$_2$-C$_{10}$ alkyl, C$_3$-C$_{10}$ cycloalkyl, C$_4$-C$_9$ alkylcycloalkyl, C$_4$-C$_9$ cycloalkylalkyl, C$_6$-C$_{10}$aryl, C$_7$-C$_{10}$alkaryl and C$_7$-C$_{10}$aralkyl;
and/or R$^3$ is selected from the group consisting of C$_1$-C$_{10}$ alkyl, C$_3$-C$_{10}$ cycloalkyl, C$_6$-C$_{10}$ aryl, C$_7$-C$_{10}$ alkaryl and C$_7$-C$_{10}$aralkyl.

3. The cyclopentane carboxylate compound according to claim 1, wherein:
R$^1$ is selected from the group consisting of methyl, ethyl and iso-butyl;
R$^2$ is selected from the group consisting of C$_2$-C$_{10}$ alkyl, C$_3$-C$_8$ cycloalkyl, C$_5$-C$_7$ cycloalkylmethyl, C$_6$-C$_9$ aryl, C$_7$-C$_{10}$ alkaryl and C$_7$-C$_{10}$ aralkyl;
and/or R$^3$ is selected from the group consisting of C$_1$-C$_4$ alkyl, C$_5$-C$_8$ cycloalkyl, phenyl, p-methylphenyl, o-methylphenyl, m-methylphenyl and benzyl.

4. The cyclopentane carboxylate compound according to claim 3, wherein R$^2$ is selected from the group consisting of C$_2$-C$_6$ alkyl, C$_5$-C$_8$ cycloalkyl, C$_6$-C$_9$ aryl, benzyl, p-methylbenzyl and phenethyl.

5. The cyclopentane carboxylate compound according to claim 3, wherein R$^1$ is methyl or ethyl; R$^2$ is selected from the group consisting of ethyl, n-propyl, iso-propyl, n-butyl, iso-butyl, n-pentyl, iso-pentyl, n-hexyl, benzyl, p-methylbenzyl and phenethyl; and/or R$^3$ is selected from the group consisting of methyl, ethyl, n-propyl, iso-propyl, n-butyl, phenyl, p-methylphenyl, o-methylphenyl, m-methylphenyl and benzyl.

6. The cyclopentane carboxylate compound according to claim 1, which is selected from the group consisting of:
ethyl 1-benzyl-2-benzoyloxy-cyclopentane carboxylate;
ethyl 1-benzyl-2-p-methylbenzoyloxy-cyclopentane carboxylate;
ethyl 1-benzyl-2-m-methylbenzoyloxy-cyclopentane carboxylate;
ethyl 1-benzyl-2-o-methylbenzoyloxy-cyclopentane carboxylate;
methyl 1-p-methylbenzyl-2-benzoyloxy-cyclopentane carboxylate;
methyl 1-p-methylbenzyl-2-p-methylbenzoyloxy-cyclopentane carboxylate;
methyl 1-p-methylbenzyl-2-m-methylbenzoyloxy-cyclopentane carboxylate;
methyl 1-p-methylbenzyl-2-o-methylbenzoyloxy-cyclopentane carboxylate;
ethyl 1-n-butyl-2-benzoyloxy-cyclopentane carboxylate;
ethyl 1-n-butyl-2-p-methylbenzoyloxy-cyclopentane carboxylate;
ethyl 1-n-hexyl-2-benzoyloxy-cyclopentane carboxylate;
ethyl 1-n-hexyl-2-p-methylbenzoyloxy-cyclopentane carboxylate;
ethyl 1-n-hexyl-2-m-methylbenzoyloxy-cyclopentane carboxylate;
ethyl 1-n-hexyl-2-o-methylbenzoyloxy-cyclopentane carboxylate;
ethyl 1-ethyl-2-acetoxy-cyclopentane carboxylate;
ethyl 1-ethyl-2-benzoyloxy-cyclopentane carboxylate;

ethyl 1-ethyl-2-o-methylbenzoyloxy-cyclopentane carboxylate;
ethyl 1-n-propyl-2-benzoyloxy-cyclopentane carboxylate;
ethyl 1-n-propyl-2-o-methylbenzoyloxy-cyclopentane carboxylate;
ethyl 1-n-propyl-2-m-methylbenzoyloxy-cyclopentane carboxylate;
ethyl 1-n-propyl-2-p-methylbenzoyloxy-cyclopentane carboxylate;
ethyl 1-n-butyl-2-m-methylbenzoyloxy-cyclopentane carboxylate;
ethyl 1-n-butyl-2-o-methylbenzoyloxy-cyclopentane carboxylate;
ethyl 1-iso-butyl-2-benzoyloxy-cyclopentane carboxylate;
ethyl 1-iso-butyl-2-o-methylbenzoyloxy-cyclopentane carboxylate;
ethyl 1-iso-butyl-2-m-methylbenzoyloxy-cyclopentane carboxylate; and
ethyl 1-iso-pentyl-2-benzoyloxy-cyclopentane carboxylate.

7. A process for preparing the cyclopentane carboxylate compound according to any one of claims 1-6, comprising, in turn, the steps of:
1) synthesizing 2-hydrocarbyl-2-hydrocarbyloxycarbonyl-cyclopentanol intermediate having a general formula (II)

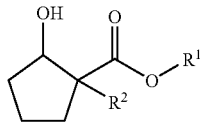

(II)

wherein
R$^1$ which can be identical or different from R$^2$ is selected from the group consisting of linear or branched C$_1$-C$_{20}$ alkyl, C$_3$-C$_{20}$ cycloalkyl, C$_6$-C$_{20}$aryl, C$_7$-C$_{20}$ alkaryl and C$_7$-C$_{20}$aralkyl and R$^2$ which can be identical or different from R$^1$ is selected from the group consisting of linear or branched C$_1$-C$_{20}$ alkyl, C$_3$-C$_{20}$ cycloalkyl, C$_6$-C$_{20}$aryl, C$_7$-C$_{20}$ alkaryl and C$_7$-C$_{20}$aralkyl, by hydrocarbylating 2-oxocyclopentane carboxylate on α-carbon with a halohydrocarbon R$^2$X in the presence of a base and an aprotic solvent to form 1-hydrocarbyl-2-oxocyclopentane carboxylate, and then selectively reducing the 1-hydrocarbyl-2-oxocyclopentane carboxylate to form 2-hydrocarbyl-2-hydrocarbyloxycarbonyl-cyclopentanol of the formula (II); and
2) synthesizing 1-hydrocarbyl-2-acyloxy-cyclopentane carboxylate compound (I) of claim 1 by acylating 2-hydrocarbyl-2-hydrocarbyloxycarbonyl-cyclopentanol of the formula (II) obtained in step 1) with an acyl halide in the presence of a base and an aprotic solvent, to form the corresponding 1-hydrocarbyl-2-acyloxy-cyclopentane carboxylate compound of the formula (I); alternatively, by acylating 2-hydrocarbyl-2-hydrocarbyloxycarbonyl-cyclopentanol of the formula (II) with a acid anhydride under acid catalytic action and in the presence of an aprotic solvent, to form corresponding 1-hydrocarbyl-2-acyloxy-cyclopentane carboxylate compound of the formula (I).

8. The process according to claim 7, wherein in the step 1), the base is selected from the group consisting of alkali metal, alkaline earth metal, hydride of alkali metal or alkaline earth metal, carbonates of alkali metal or alkaline earth metal, and combinations thereof;
and/or the aprotic solvent is selected from the group consisting of: acetone, dimethyl sulfoxide, N,N-dimethyl formamide, tetrahydrofuran, pentane, hexane, benzene, toluene, xylene, and combinations thereof.

9. The process according to claim 8, wherein in the step 1), the aprotic solvent is N,N-dimethyl formamide, and/or the base is a carbonate of an alkali metal.

10. The process according to claim 7, wherein in the step 1), benzyl triethyl ammonium chloride or tetra-n-butyl ammonium bromide or a combination thereof as phase-transfer catalyst is used when the halohydrocarbon used in the hydrocarbylation on α-carbon is a branched or a cyclic group-containing haloalkane.

11. The process according to claim 7, wherein in the step 1), 1-hydrocarbyl-2-oxocyclopentane carboxylate is reduced with a reducing agent, which is selected from the group consisting of: lithium borohydride, sodium borohydride, potassium borohydride, zinc borohydride, aluminum alkoxides, and combinations thereof, in an alcoholic solvent.

12. The process according to claim 11, wherein the reducing agent and the solvent are respectively sodium borohydride and methanol; or aluminum isopropoxide and isopropanol.

13. The process according to claim 7, wherein the 1-hydrocarbyl-2-oxocyclopentane carboxylate is selectively reduced under conditions of catalytic hydrogenation, with the catalyst being selected from the group consisting of:
nickel-containing catalysts, palladium-containing catalysts, an Adams' catalyst, and ruthenium-containing catalysts.

14. The process according to claim 7, wherein in the step 2), the base is selected from the group consisting of: pyridine, triethylamine, and a combination thereof;
and/or the aprotic solvent is selected from the group consisting of: pyridine, tetrahydrofuran, methylene chloride, chloroform, pentane, hexane, benzene, toluene, xylene, and combinations thereof.

15. The process according to claim 7, wherein in the hydrocarbylation on α-carbon of the step 1), the molar ratio of the 2-oxocyclopentane carboxylate to the halohydrocarbon is in a range of from 1:0.5 to 1:5,
and/or th molar ratio of the 2-oxocyclopentane carboxylate to the base is in a range of from 1:0.5 to 1:5.

16. The process according to claim 7, wherein in the hydrocarbylation on α-carbon of the step 1), the reaction pressure is in a range of from atmosphere pressure to 3 atm, the reaction temperature is in a range of from 10 to 190° C., and/or the reaction time is in a range of from 1 to 24 hours.

17. The process according to claim 11, wherein in the reduction reaction of the step 1), the molar ratio of the 1-hydrocarbyl-2-oxocyclopentane carboxylate to the reducing agent is in a range of from 1:0.5 to 1:2; the reaction pressure is in a range of from atmosphere pressure to 3 atm; the reaction temperature is in a range of from −20 to 100° C.; and/or the reaction time is in a range of from 0.1 to 10 hours.

18. The process according to claim 7, wherein the reduction of the step 1) is carried out under conditions of catalytic hydrogenation, wherein the reaction pressure is in a range of from 1 to 10 atm; the reaction temperature is in a range of from 0 to 200° C.; the reaction time is in a range of from 0.5 to 24 hours; the solvent is selected from the group consisting of alcohols, ethers, esters, and combinations thereof; and/or the catalyst is used in an amount of from 0.1 to 5 percent by mole with respect to the reactant 1-hydrocarbyl-2-oxocyclopentane carboxylate.

19. The process according to claim 7, wherein in the step 2), an acyl halide is used as acylating agent, and the molar ratio of the acylating agent to the intermediate (II) is in a range of from 1:1 to 15:1; the molar ratio of base to the acylating agent is in a range of from 1:1 to 10:1; the reaction temeperature is in a range of from −20 to 200° C.;
and/or reaction pressure is in a range of from atmospheric pressure to 3 atm.

* * * * *